United States Patent
Kamei

(10) Patent No.: US 10,662,294 B2
(45) Date of Patent: May 26, 2020

(54) ORGANOPOLYSILOXANE, COSMETICS, AND METHOD FOR MANUFACTURING ORGANOPOLYSILOXANE

(71) Applicant: SHIN-ETSU CHEMICAL CO., LTD., Tokyo (JP)

(72) Inventor: Masanao Kamei, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 14 days.

(21) Appl. No.: 16/082,739

(22) PCT Filed: Feb. 20, 2017

(86) PCT No.: PCT/JP2017/006150
§ 371 (c)(1),
(2) Date: Sep. 6, 2018

(87) PCT Pub. No.: WO2017/169278
PCT Pub. Date: Oct. 5, 2017

(65) Prior Publication Data
US 2019/0077920 A1 Mar. 14, 2019

(30) Foreign Application Priority Data

Mar. 28, 2016 (JP) .................................. 2016-064626
Apr. 6, 2016 (JP) .................................. 2016-076387

(51) Int. Cl.
| | | |
|---|---|---|
| C08G 77/46 | (2006.01) | |
| C08G 77/48 | (2006.01) | |
| A61K 8/894 | (2006.01) | |
| A61Q 17/04 | (2006.01) | |
| A61Q 1/02 | (2006.01) | |
| A61K 8/892 | (2006.01) | |
| C08K 5/56 | (2006.01) | |
| C08G 77/38 | (2006.01) | |
| C08K 5/06 | (2006.01) | |
| C08G 77/12 | (2006.01) | |
| A61Q 1/10 | (2006.01) | |
| C08G 77/00 | (2006.01) | |
| A61Q 19/00 | (2006.01) | |
| A61Q 1/00 | (2006.01) | |
| A61K 8/891 | (2006.01) | |
| C08G 77/50 | (2006.01) | |
| A61K 8/06 | (2006.01) | |
| A61K 8/92 | (2006.01) | |

(52) U.S. Cl.
CPC ............. *C08G 77/46* (2013.01); *A61K 8/891* (2013.01); *A61K 8/892* (2013.01); *A61K 8/894* (2013.01); *A61Q 1/00* (2013.01); *A61Q 1/02* (2013.01); *A61Q 1/10* (2013.01); *A61Q 17/04* (2013.01); *A61Q 19/00* (2013.01); *C08G 77/12* (2013.01); *C08G 77/38* (2013.01); *C08G 77/48* (2013.01); *C08G 77/50* (2013.01); *C08G 77/80* (2013.01); *C08K 5/06* (2013.01); *C08K 5/56* (2013.01); *A61K 8/06* (2013.01); *A61K 8/92* (2013.01)

(58) Field of Classification Search
CPC ...................................................... C08G 77/46
See application file for complete search history.

(56) References Cited

U.S. PATENT DOCUMENTS

| | | | |
|---|---|---|---|
| 4,431,789 A | 2/1984 | Okazaki et al. | |
| 6,576,623 B1 | 6/2003 | Nakanishi et al. | |
| 7,771,709 B2 | 8/2010 | Nakanishi et al. | |
| 8,080,239 B2 * | 12/2011 | Matsuo ............... | A61K 31/695 424/401 |
| 2005/0008600 A1 | 1/2005 | Nakanishi et al. | |

(Continued)

FOREIGN PATENT DOCUMENTS

| | | |
|---|---|---|
| EP | 2505602 A1 | 10/2012 |
| EP | 2837649 A1 | 2/2015 |

(Continued)

OTHER PUBLICATIONS

Mar. 14, 2017 International Search Report issued in International Patent Application No. PCT/JP2017/006150.
Oct. 2, 2018 International Preliminary Report on Patentability issued in International Patent Application No. PCT/JP2017/006150.
Oct. 1, 2019 Extended European Search Report issued in European Patent Application No. 17773826.7.

*Primary Examiner* — Marc S Zimmer
(74) *Attorney, Agent, or Firm* — Oliff PLC

(57) ABSTRACT

An organopolysiloxane that can suppress swelling of a container due to a hydrogen gas derived from Si—H groups and occurrence of an offensive odor derived from aliphatic unsaturated groups, and that is excellent in emulsification stability and has good cosmetic durability, and a cosmetic containing the same. The organopolysiloxane being represented by the following average formula (1):

(1)

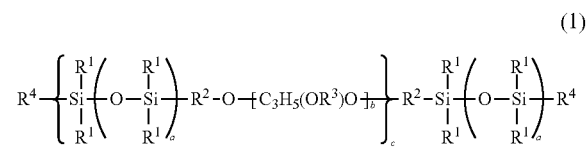

wherein, R1 represents a group selected from an alkyl group having 1 to 30 carbon atoms, etc., R2 represents a divalent organic group having 2 to 15 carbon atoms, R3 represents any of a hydrogen atom and an alkyl group having 1 to 30 carbon atoms, R4s each independently represent a group selected from an alkyl group having 2 to 30 carbon atoms and another organopolysiloxane, "a" is 1 to 500, "b" is 1 to 10, and "c" is 1 to 10.

11 Claims, No Drawings

(56) References Cited

U.S. PATENT DOCUMENTS

| | | |
|---|---|---|
| 2012/0252757 A1 | 10/2012 | Kamei |
| 2013/0150458 A1 | 6/2013 | Iyoku |
| 2015/0004107 A1* | 1/2015 | Sawayama ............ A61K 8/892 424/59 |
| 2015/0050498 A1 | 2/2015 | Inokuchi |
| 2016/0177038 A1* | 6/2016 | Hori .................... C08G 77/14 514/772.1 |

FOREIGN PATENT DOCUMENTS

| | | | |
|---|---|---|---|
| JP | S62-034039 | B2 | 7/1987 |
| JP | H04-015762 | B2 | 3/1992 |
| JP | H04-020407 | B2 | 4/1992 |
| JP | H05-012979 | B2 | 2/1993 |
| JP | H05-013126 | B2 | 2/1993 |
| JP | H06-062385 | B2 | 8/1994 |
| JP | 3283277 | B2 | 5/2002 |
| JP | 2005-042097 | A | 2/2005 |
| JP | 2005-089340 | A | 4/2005 |
| JP | 3724988 | B2 | 12/2005 |
| JP | 2007-161650 | A | 6/2007 |
| JP | 3976226 | B2 | 9/2007 |
| JP | 4442883 | B2 | 3/2010 |
| JP | 2010-120914 | A | 6/2010 |
| JP | 4567584 | B2 | 10/2010 |
| JP | 2012-207078 | A | 10/2012 |
| JP | 5037782 | B2 | 10/2012 |
| JP | 2013-028745 | A | 2/2013 |
| JP | 2013-119596 | A | 6/2013 |
| JP | 5795212 | B2 | 10/2015 |
| WO | WO 2014/200211 | * | 12/2014 |

* cited by examiner

ORGANOPOLYSILOXANE, COSMETICS, AND METHOD FOR MANUFACTURING ORGANOPOLYSILOXANE

TECHNICAL FIELD

The present invention relates to an organopolysiloxane, a cosmetic, and a method for manufacturing the organopolysiloxane.

BACKGROUND ART

Silicone oil has been used as an oil in various fields for its safety, etc. In cosmetics, it has also been frequently used, and in the uses such as skin care, makeup cosmetics, etc., in particular, silicone oil having low dynamic viscosity of 100 mm$^2$/sec or less has widely been used due to its excellent extensibility, refreshing feeling and safety.

Silicone oil is often used as an emulsified product in applications such as cosmetics, etc., and in such a case, a silicone-based surfactant is frequently used. As the silicone-based surfactant, a polyether-modified silicone having a polyoxyalkylene group at the terminal or side chain of siloxane, for example, Patent Documents 1 to 5, etc., have been known.

Further, there have been known Patent Document 6 as a polyether-modified silicone in which a siloxane part of a main chain has been branched, Patent Document 7 as an ABA type copolymer shown by the following formula,

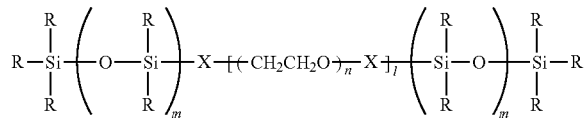

(Wherein, X is an arbitrary linking group, and urethane, urea, amide, ester and alkyl ether are exemplified. Also, regardless of other descriptions, R is a linear or branched alkylene group each having 1 to 12 carbon atoms, or a phenyl group, "l" is 1 to 5, "m" is 40 to 90, and "n" is 10 to 40.)

moreover, Patent Document 8 as a block copolymer shown by the following formula,

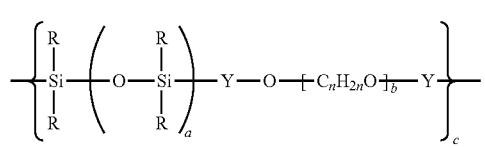

(Wherein, Y is a divalent organic group one end of which is bonded to a silicon atom and the other of which is bonded to an oxygen atom. Also, regardless of other descriptions, R is a monovalent hydrocarbon group containing no aliphatic unsaturated group, "a" is 6 or more, "b" is 4 or more, "c" is 2 or more, and "n" is 2, 3 or 4.)

and Patent Document 9 as a copolymer in which a polyether group shown by the following formula has been grafted.

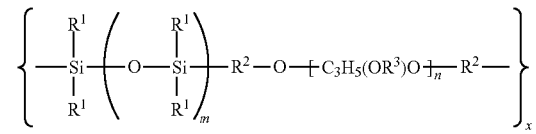

(Wherein, regardless of other descriptions, at least one among "n" of R$^3$s is a polyoxyalkylene. Also, R$^1$s are, each independently, a group selected from an alkyl group having 1 to 30 carbon atoms, etc., R$^2$ is a divalent organic group having 2 to 15 carbon atoms which may have an oxygen atom(s), and R$^3$ is a group selected from a polyoxyalkylene and hydrogen. "m" is a number of 0 to 500, "n" is a number of 1 to 10, and "x" is a number of 2 or more.)

There have also been known Patent Document 10 which discloses a silicone having a (poly)glycerin group as the other hydrophilic group, Patent Document 11 in which siloxane part is branched, Patent Document 12 as an ABA type copolymer such as a material shown by the following formula,

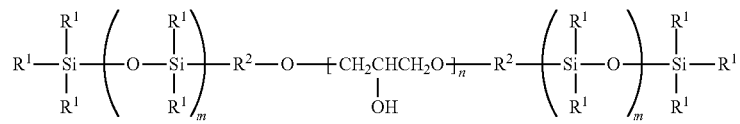

(Wherein, regardless of other descriptions, R$^2$ represents an alkylene group having 2 to 11 carbon atoms, R$^1$ represents a linear or branched alkyl group having 1 to 12 carbon atoms, or a phenyl group, "m" is 10 to 120, and "n" is 1 to 11.)

and further, Patent Document 13 as a block copolymer shown by the following formula.

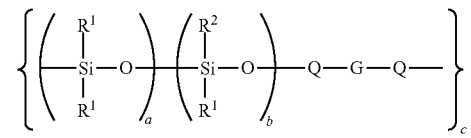

(Wherein, Q represents a divalent organic group having 3 to 20 carbon atoms which may contain an ether bond and an ester bond, G is made a monoglycerin or polyglycerin residue. Also, regardless of other descriptions, R$^1$ represents an alkyl group having 1 to 10 carbon atoms, an aryl group, an aralkyl group, an amino-substituted alkyl group, a carboxyl-substituted alkyl group, $R^2$ represents an alkyl group having 11 to 30 carbon atoms, "a" is an integer of 2 or more and 100 or less, "b" is an integer of 0 or more and 100 or less, and "c" is an integer of 2 or more and 100 or less.)

The silicone-based surfactants are used, depending on the purpose, with regard to a kind of the hydrophilic group, a binding site, balance in the hydrophilic group/lipophilic group (silicone), etc., respectively. The block copolymer of Patent Document 13 is synthesized by an addition polymerization reaction of an organopolysiloxane having Si—H groups at the both terminals and a derivative having 2 mol of aliphatic unsaturated bonds in one molecule, but it becomes a derivative having a Si—H group or an aliphatic unsaturated bond at the terminal thereof. There are disadvantages that in the case where the Si—H groups remain, hydrogen is by-produced by dehydrogenation reaction with a lapse of time, so that a container is swelled, and in the case where a derivative has an aliphatic unsaturated bond, offensive odor derived from the aliphatic unsaturated group is generated with a lapse of time.

CITATION LIST

Patent Literature

Patent Document 1: JP Hei.04-15762 B2
Patent Document 2: JP Hei.04-20407 B2
Patent Document 3: JP Hei.05-13126 B2
Patent Document 4: JP Hei.06-62385 B2
Patent Document 5: JP Hei.05-12979 B2
Patent Document 6: JP Patent No. 3724988
Patent Document 7: JP Patent No. 4442883
Patent Document 8: JP Patent No. 3283277
Patent Document 9: JP Patent No. 5795212
Patent Document 10: JP Sho.62-34039 B2
Patent Document 11: JP Patent No. 3976226
Patent Document 12: JP Patent No. 4567584
Patent Document 13: JP Patent No. 5037782

SUMMARY OF THE INVENTION

Technical Problem

The present invention has been made in view of the above problems, and it is an object of the present invention to provide an organopolysiloxane which can provide a cosmetic, which can suppress swelling of a container due to a hydrogen gas derived from Si—H groups and occurrence of an offensive odor derived from aliphatic unsaturated groups with a lapse of time, is excellent in emulsification stability and has good cosmetic durability, and a cosmetic containing the same. It is also an object to provide a method for manufacturing such an organopolysiloxane.

Solution to Problem

In order to accomplish the objects, in the present invention, an organopolysiloxane represented by the following average formula (1) is provided.

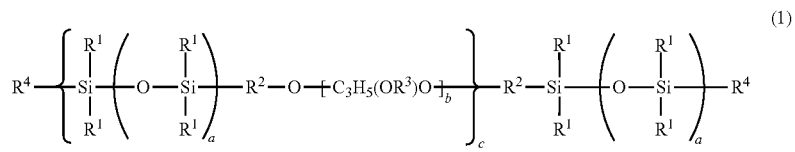

[Wherein, $R^1$s each independently represent a group selected from an alkyl group having 1 to 30 carbon atoms, a fluorine-substituted alkyl group having 1 to 30 carbon atoms, an aryl group having 6 to 30 carbon atoms, and an aralkyl group having 7 to 30 carbon atoms, $R^2$ represents a divalent organic group having 2 to 15 carbon atoms which may have an oxygen atom(s), $R^3$ represents any of a hydrogen atom and an alkyl group having 1 to 30 carbon atoms, $R^4$s each independently represent a group selected from an alkyl group having 2 to 30 carbon atoms and an organopolysiloxane represented by the following average formula (2), "a" is 1 to 500, "b" is 1 to 10, and "c" is 1 to 10. Provided that when "c" is 1, $R^4$s each independently represent an alkyl group having 14 to 30 carbon atoms or an organopolysiloxane represented by the following average formula (2).

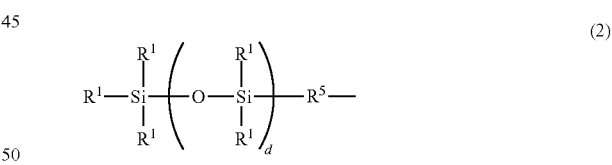

(Wherein, $R^1$ has the same meaning as defined above, $R^5$ represents a divalent organic group having 2 to 15 carbon atoms, and "d" is 1 to 500.)]

When such an organopolysiloxane is employed, a cosmetic which can suppress swelling of a container due to a hydrogen gas derived from Si—H groups and occurrence of an offensive odor derived from aliphatic unsaturated groups with a lapse of time, is excellent in emulsification stability and has good cosmetic durability can be provided.

Also, the organopolysiloxane of the present invention is preferably an organopolysiloxane represented by the following average formula (3).

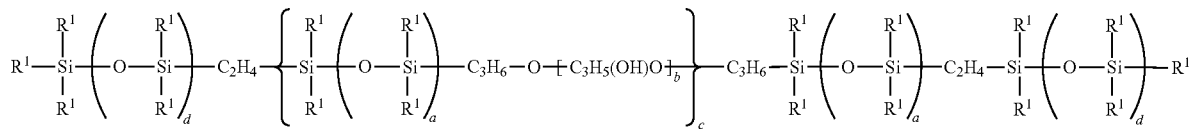

(3)

[Wherein, $R^1$, "a", "b", "c", and "d" have the same meanings as defined above.]

When such an organopolysiloxane is employed, it can be easily manufactured, and a manufacturing cost can be suppressed.

Further, in the present invention, it is provided a cosmetic which comprises the organopolysiloxane of the present invention in an amount of 0.1 to 40% by mass based on a total mass of the cosmetic.

When such a cosmetic is employed, it becomes a cosmetic which can suppress swelling of a container due to a hydrogen gas derived from Si—H groups and occurrence of an offensive odor derived from aliphatic unsaturated groups with a lapse of time, is excellent in emulsification stability and has good cosmetic durability.

Also, the cosmetic may further contain water and may be in the form of an emulsion.

In addition, the cosmetic further contain either of silicone oil, ester oil, glyceride oil, or a mixture thereof, and may be in the form of a nonaqueous emulsion.

Thus, the cosmetic of the present invention can be in various forms depending on various kinds of the cosmetics.

Further, the cosmetic may further contain powder, and, may be either of the forms such as a liquid, past and solid, into which the powder has been dispersed.

The cosmetic containing the organopolysiloxane of the present invention does not change such as agglomeration of powder, etc., and excellent in dispersion stability of powder, even when it contains powder. In addition, when it is either of the forms such as a liquid, past and solid, handling property is good and it can be applied to various cosmetics.

Further, in the present invention, it is provided a method for manufacturing an organopolysiloxane represented by the following average formula (1), which comprises subjecting to addition reaction of a dialkenyl(poly)glycerin compound and a both terminal-hydrogen polysiloxane in the presence of a catalyst, under a condition that an amount of Si—H groups contained in the both terminal-hydrogen polysiloxane is in excess of an amount of alkenyl groups contained in the dialkenyl(poly)glycerin compound, and subjecting to addition reaction of the Si—H group existing at the both terminals of the product obtained by the reaction, and one or more kinds selected from an α-olefin and an organopolysiloxane having an alkenyl group at one terminal thereof, in the presence of a catalyst.

[Wherein, $R^1$s each independently represent a group selected from an alkyl group having 1 to 30 carbon atoms, a fluorine-substituted alkyl group having 1 to 30 carbon atoms, an aryl group having 6 to 30 carbon atoms, and an aralkyl group having 7 to 30 carbon atoms, $R^2$ represents a divalent organic group having 2 to 15 carbon atoms which may have an oxygen atom(s), $R^3$ represents any of a hydrogen atom and an alkyl group having 1 to 30 carbon atoms, $R^4$s each independently represent a group selected from an alkyl group having 2 to 30 carbon atoms and an organopolysiloxane represented by the following average formula (2), "a" is 1 to 500, "b" is 1 to 10, and "c" is 1 to 10. Provided that when "c" is 1, $R^4$s each independently represent an alkyl group having 14 to 30 carbon atoms or an organopolysiloxane represented by the following average formula (2).

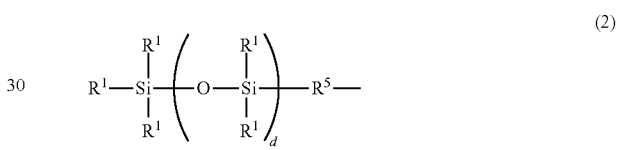

(2)

(wherein, $R^1$ has the same meaning as defined above, $R^5$ represents a divalent organic group having 2 to 15 carbon atoms, and "d" is 1 to 500.)]

When such a method for manufacturing an organopolysiloxane is employed, it is possible to certainly manufacture an organopolysiloxane which can provide a cosmetic, which can suppress swelling of a container due to a hydrogen gas derived from Si—H groups and occurrence of an offensive odor derived from aliphatic unsaturated groups with a lapse of time, is excellent in emulsification stability and has good cosmetic durability.

Advantageous Effects of Invention

The organopolysiloxane of the present invention can form a cosmetic which can suppress swelling of a container due to a hydrogen gas derived from Si—H groups and occurrence of an offensive odor derived from aliphatic unsaturated groups with a lapse of time, and is excellent in emulsification stability and cosmetic durability.

DESCRIPTION OF EMBODIMENTS

In the following, the present invention is explained in more detail.

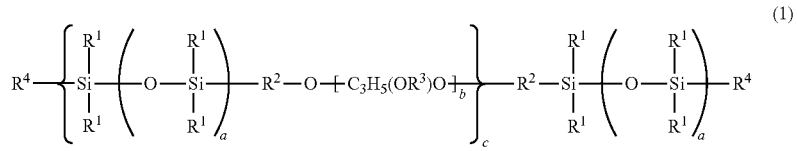

(1)

As described above, it has been desired to obtain an organopolysiloxane which can provide a cosmetic, which can suppress swelling of a container due to a hydrogen gas derived from Si—H groups and occurrence of an offensive odor derived from aliphatic unsaturated groups, is excellent in emulsification stability and has good cosmetic durability.

The present inventors have intensively studied to accomplish the objects mentioned above. As a result, they have found that the organopolysiloxane represented by the following average formula (1) can solve the problems mentioned above to accomplish the present invention.

In the following, embodiments of the present invention are specifically explained, but the present invention is not limited by these.

The organopolysiloxane of the present invention is a material represented by the following average formula (1).

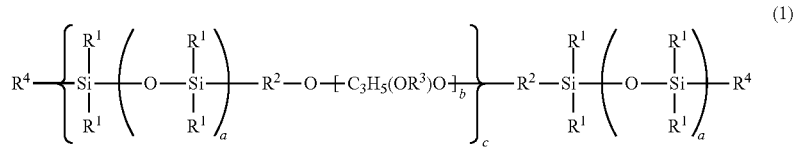

(1)

In the formula (1), $R^1$s each independently represent a group selected from an alkyl group having 1 to 30 carbon atoms, a fluorine-substituted alkyl group having 1 to 30 carbon atoms, an aryl group having 6 to 30 carbon atoms, and an aralkyl group having 7 to 30 carbon atoms. As the alkyl group having 1 to 30 carbon atoms, there may be exemplified by an alkyl group such as a methyl group, an ethyl group, a propyl group, a butyl group, a pentyl group, a hexyl group, a heptyl group, an octyl group, a nonyl group, a decyl group, a dodecyl group, a tetradecyl group, a hexadecyl group, an octadecyl group, etc., and a cycloalkyl group such as a cyclopentyl group, a cyclohexyl group, etc. As the fluorine-substituted alkyl group having 1 to 30 carbon atoms, there may be exemplified by a trifluoropropyl group, a heptadecafluorodecyl group, etc., as the aryl group having 6 to 30 carbon atoms, a phenyl group and a tollyl group, and as the aralkyl group having 7 to 30 carbon atoms, a benzyl group, and a phenethyl group, etc.

It is preferable that $R^1$ is an alkyl group having 1 to 15 carbon atoms, or a phenyl group, more preferably selected from a methyl group and a butyl group. Further, 50% or more of $R^1$ is preferably a methyl group, and most preferably 70% or more of $R^1$ is a methyl group.

$R^2$ is a divalent organic group having 2 to 15 carbon atoms which may have an oxygen atom(s). As the divalent organic group having 2 to 15 carbon atoms which may have an oxygen atom(s) of $R^2$, there may be exemplified by an alkylene group having 2 to 15 carbon atoms such as —(CH$_2$)$_2$—, —(CH$_2$)$_3$—, —(CH$_2$)$_4$—, —CH$_2$CH(CH$_3$)CH$_2$—, —(CH$_2$)$_8$—, —(CH$_2$)$_{11}$—, etc., and an oxyalkylene group having 2 to 15 carbon atoms such as —(CH$_2$)$_3$—O—(CH$_2$)$_2$—, —(CH$_2$)$_2$—O—(CH$_2$)$_3$—, etc., and preferably —(CH$_2$)$_2$—, —(CH$_2$)$_3$—, or —CH$_2$CH(CH$_3$) CH$_2$—.

$R^3$ is any of a hydrogen atom and an alkyl group having 1 to 30 carbon atoms. As the alkyl group having 1 to 30 carbon atoms of $R^3$, there may be exemplified by a methyl group, an ethyl group, a propyl group, a butyl group, a pentyl group, a hexyl group, a heptyl group, an octyl group, a nonyl group, a decyl group, a dodecyl group, a tetradecyl group, a hexadecyl group, an octadecyl group, etc. It is preferred that $R^3$ is a hydrogen atom.

$R^4$s each independently represent a group selected from an alkyl group having 2 to 30 carbon atoms and an organopolysiloxane represented by the following average formula (2). As the alkyl group having 2 to 30 carbon atoms of $R^4$, there may be exemplified by an alkyl group such as an ethyl group, a propyl group, a butyl group, a pentyl group, a hexyl group, a heptyl group, an octyl group, a nonyl group, a decyl group, a dodecyl group, a tetradecyl group, a hexadecyl group, an octadecyl group, etc. The organopolysiloxane of $R^4$ is represented by the following average formula (2).

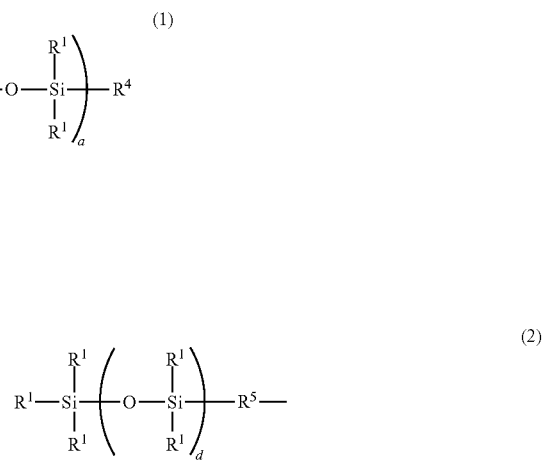

(2)

In the formula (2), $R^1$ has the same meaning as defined above, and $R^5$ is a divalent organic group having 2 to 15 carbon atoms. As the divalent organic group having 2 to 15 carbon atoms of $R^5$, there may be exemplified by an alkylene group having 2 to 15 carbon atoms such as —(CH$_2$)$_2$—, —(CH$_2$)$_3$—, —(CH$_2$)$_4$—, —CH$_2$CH(CH$_3$)CH$_2$—, —(CH$_2$)$_8$—, —(CH$_2$)$_{11}$—, etc.

It is preferable that $R^4$ is a hexyl group, an octyl group, a dodecyl group, an octadecyl group, or the organopolysiloxane represented by the formula (2).

In the formula (1), "a" is 1 to 500, preferably 1 to 250, and more preferably 1 to 150. "b" is 1 to 10, preferably 1 to 6, and more preferably 2 to 5. "c" is 1 to 10, preferably 2 to 10, and more preferably 2 to 5. Provided that when "c" is 1, $R^4$s each independently represent an alkyl group having 14 to 30 carbon atoms or an organopolysiloxane represented by the following average formula (2).

In the formula (2), "d" is 1 to 500, preferably 1 to 250, and more preferably 1 to 150.

Also, a molecular weight of the organopolysiloxane of the present invention is preferably 500 to 500,000, more preferably 1,000 to 100,000, and particularly preferably 2,000 to 50,000 with a number average molecular weight in terms of polystyrene by GPC (gel permeation chromatography).

The novel block type organopolysiloxane having a (poly) glycerin group of the present invention has no Si—H group and aliphatic unsaturated group at both terminals, so that it can provide a cosmetic which can suppress swelling of a container due to a hydrogen gas derived from Si—H groups and occurrence of an offensive odor derived from aliphatic unsaturated groups with a lapse of time, is excellent in emulsification stability and has good cosmetic durability.

As the organopolysiloxane represented by the average formula (1), there may be preferably mentioned, for example, an organopolysiloxane represented by the following average formula (3). Such an organopolysiloxane can be easily manufactured and the manufacturing cost can be suppressed.

Incidentally, the reaction products of 2 mol of allyl glycidyl ether and glycerin are materials having the OH group(s), and the hydrogen atom(s) in the OH group(s) may be substituted by an alkyl group having 1 to 30 carbon atoms, if necessary. In this case, instead of glycerin, the hydrogen atom(s) in the OH group(s) can be substituted with (3)

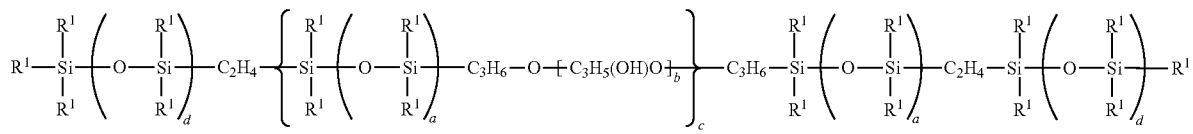

[Wherein, $R^1$, "a", "b", "c", and "d" have the same meanings as defined above.]

The organopolysiloxane represented by the average formula (1) of the present invention can be synthesized by the following method.

(Step 1: Synthesis of Dialkenyl(Poly)Glycerin Compound)

An epoxy compound such as monoalkenyl glycidyl ether, glycidol, etc., and a compound having a hydroxyl group(s) such as glycerin, diglycerin, triglycerin, glycerin monoallyl ether, etc., are subjected to ring-opening reaction of the epoxy in the presence of an alkali catalyst to synthesize a (poly)glycerin compound having two alkenyl groups. By changing the formulation molar ratio of each raw material, compounds with various polymerization degrees can be synthesized. Incidentally, the alkenyl group(s) in the dialkenyl(poly)glycerin compound may be bonded to the (poly)glycerin chain through the divalent organic group.

The ring-opening reaction of the hydroxyl group and the epoxy in Step 1 is conventionally known. As the alkali catalyst, KOH, NaOH, NaOCH$_3$, etc., are used, and an addition amount of the alkali catalyst is usually 0.2 to 2 mol %, preferably 0.2 to 1 mol % based on the OH group-containing compound.

Since the reaction of Step 1 is a ring-opening reaction of the epoxy, various isomers of a branched structure or a cyclic structure may be formed depending on the formulation composition of each raw material at the time of this reaction. When an example is shown, in the reaction of 2 mol of allyl glycidyl ether and glycerin, the product becomes a mixture containing the following as isomers.

an alkyl group having 1 to 30 carbon atoms by the reaction of glycerin alkyl ether and allyl glycidyl ether.

(Step 2: Synthesis of (Poly)Glycerin Compound Having Si—H Groups at Both Terminals)

The dialkenyl(poly)glycerin compound obtained in Step 1 and both terminal-hydrogen polysiloxane are subjected to addition reaction in the presence of a catalyst under the condition that an amount of the Si—H group contained in the both terminal-hydrogen polysiloxane is in excess of the alkenyl group contained in the dialkenyl(poly)glycerin compound. According to this procedure, a (poly)glycerin compound having a Si—H group at both terminals is synthesized. For example, it is preferable that 1.05 to 2.0 mol of a both terminal-hydrogen polysiloxane (polysiloxane having two Si—H groups) is reacted with 1 mol of the dialkenyl (poly)glycerin compound ((poly)glycerin compound having two alkenyl groups).

The (poly)glycerin compound obtained in Step 2 is a material in which Si—H group is remained at the both terminals, so that there was a defect that hydrogen was by-produced by dehydrogenation reaction with a lapse of time and the container swelled. Thus, in the present invention, Step 3 is carried out to suppress this defect, i.e., to eliminate the Si—H group remained at the both terminals.

(Step 3: Synthesis of Organopolysiloxane Represented by the Average Formula (1))

The Si—H group existing at the both terminals of the product obtained by the addition reaction of Step 2, and one or more kinds selected from an α-olefin and an organopolysiloxane having an alkenyl group at one of the terminals thereof are subjected to addition reaction in the presence of

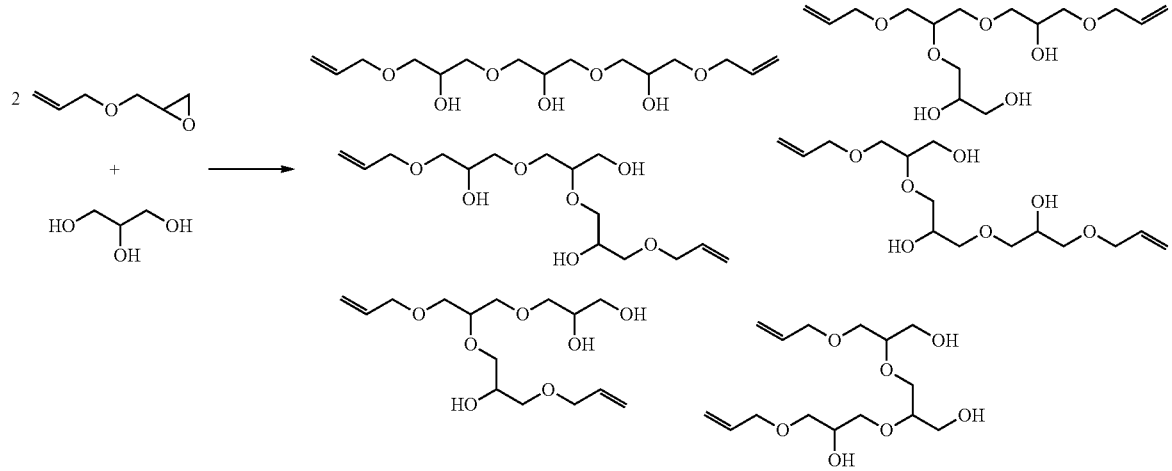

a catalyst. According to this procedure, the organopolysiloxane represented by the average formula (1) is synthesized. For example, it is preferable that 1 to 5 mol of one or more kinds selected from an α-olefin and an organopolysiloxane having an alkenyl group at one of the terminals thereof is reacted with 1 mol of the product obtained by the addition reaction of Step 2.

The addition reactions of Steps 2 and 3 are desirably carried out in the presence of a platinum catalyst or a rhodium catalyst and, for example, chloroplatinic acid, alcohol-modified chloroplatinic acid, chloroplatinic acid-vinylsiloxane complex, etc., are suitably used. Incidentally, an amount of the catalyst to be used may be an amount effective as a catalyst, and is usually 50 ppm or less, preferably 20 ppm or less in terms of an amount of platinum or rhodium.

The addition reactions of Steps 2 and 3 may be carried out in an organic solvent, if necessary, and as the organic solvent, there may be exemplified by, for example, an aromatic hydrocarbon such as toluene, xylene, etc., a lower alcohol such as ethanol, isopropyl alcohol, etc., an aliphatic or an alicyclic hydrocarbon such as n-pentane, n-hexane, cyclohexane, etc., a halogenated hydrocarbon such as dichloromethane, chloroform, carbon tetrachloride, etc., an ether such as tetrahydrofuran, dioxane, etc., and a ketone such as acetone, methyl ethyl ketone, etc. A hydrocarbon solvent or a lower alcohol is preferably used.

The addition reactions of Steps 2 and 3 can be carried out continuously. For example, after subjecting to addition reaction of Step 2 by adding raw materials, etc., of Step 2 to the reactor, an α-olefin, etc., are added to the solution after completion of the reaction whereby the addition reaction of Step 3 can be carried out. When such a method is employed, it is not necessary to add the catalyst again so that it is efficient.

A heating temperature and a heating time in the addition reactions of Steps 2 and 3 are not particularly limited, and in the case of using a solvent, it is preferable to carry out the reaction for 1 to 10 hours under the reflux thereof. A total of the heating time in the addition reactions of Steps 2 and 3 is not particularly limited, and it can be made 2 to 20 hours.

According to the manufacturing method of the organopolysiloxane of the present invention, an organopolysiloxane which can provide a cosmetic, which can suppress swelling of a container due to a hydrogen gas derived from Si—H groups and occurrence of an offensive odor derived from aliphatic unsaturated groups with a lapse of time, is excellent in emulsification stability and has good cosmetic durability, can be certainly manufactured.

The organopolysiloxane of the present invention is suitably used in cosmetics externally used for the skin or hair. In particular, it is suitable as an emulsifier for cosmetics containing silicone which is commonly used in cosmetics, and a polar solvent such as water, glycol, ester oil, glyceride oil, etc. A formulation amount of the organopolysiloxane when it is used for the cosmetic is preferably in the range of 0.1 to 40% by mass, further 0.5 to 20% by mass based on the total mass of the cosmetic.

In the cosmetic of the present invention, one kind or two or more kinds of oils may be formulated depending on the purpose. Any oils of solid, semi-solid or liquid can be used as long as it is used in ordinary cosmetics, and, for example, natural animal and vegetable oils and fats and semisynthetic oils and fats, hydrocarbon oils, higher fatty acids, higher alcohols, ester oils, glyceride oils, conventionally used silicone oils, and fluorine-based oils can be used.

As the natural animal and vegetable oils and fats and semisynthetic oils and fats, there may be exemplified by, for example, avocado oil, linseed oil, almond oil, insects wax, perilla oil, olive oil, cacao butter, kapok wax, kaya oil, carnauba wax, liver oil, candelilla wax, purified candelilla wax, beef tallow, neats foot fat, beef bone fat, hardened beef tallow, apricot kernel oil, whale wax, hardened oil, wheat germ oil, sesame oil, rice germ oil, rice bran oil, sugarcane wax, *Camellia* sasanqua oil, safflower oil, Shea butter, Chinese tung oil, cinnamon oil, jojoba wax, squalane, squalene, shellac wax, turtle oil, soybean oil, tea seed oil, *camellia* oil, evening primrose oil, corn oil, lard, rapeseed oil, Japanese tung oil, bran wax, germ oil, horse fat, persic oil, palm oil, palm kernel oil, castor oil, hardened castor oil, castor oil fatty acid methyl ester, sunflower oil, grape oil, bayberry wax, jojoba oil, macadamia nut oil, bees wax, mink oil, meadowfoam oil, cottonseed oil, cotton wax, Japan wax, Japan wax kernel oil, montan wax, coconut oil, hardened coconut oil, tri-coconut oil fatty acid glyceride, mutton tallow, peanut oil, lanolin, liquid lanolin, reduced lanolin, lanolin alcohol, hard lanolin, lanolin acetate, acetylated lanolin alcohol, lanolin fatty acid isopropyl, POE lanolin alcohol ether, POE lanolin alcohol acetate, lanolin fatty acid polyethylene glycol, POE hydrogenated lanolin alcohol ether, egg yolk oil, etc.

Provided that POE means polyoxyethylene (hereinafter the same).

As the hydrocarbon oils, there may be exemplified by a linear, branched, and further volatile hydrocarbon oils, etc., and specifically mentioned, ozokerite, α-olefin oligomer, light isoparaffin, isododecane, isohexadecane, light liquid isoparaffin, squalane, synthetic squalane, vegetable squalane, squalene, ceresin, paraffin, paraffin wax, polyethylene wax, polyethylene•polypropylene wax, an (ethylene/propylene/styrene) copolymer, a (butylene/propylene/styrene) copolymer, liquid paraffin, liquid isoparaffin, pristane, polyisobutylene, hydrogenated polyisobutene, microcrystalline wax, vaseline, etc.; and as the higher fatty acid, there may be exemplified by lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, etc.

As the higher alcohol, there may be exemplified by lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterol, POE cholesterol ether, monostearyl glycerin ether (batyl alcohol), monooleyl glyceryl ether (selacyl alcohol), etc.

As the ester oil, there may be exemplified by diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanate, isotridecyl isononanate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, N-lauroyl-L-glutamic acid-2-octyldodecyl ester, isopropyl lauroyl sarcosinate, diisostearyl malate, etc.; and as the glyceride oil, there may be exemplified by acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, diglyceryl isostearate/myristate, etc.

As the silicone oil, there may be exemplified by a linear or branched organopolysiloxane of low viscosity to high viscosity such as dimethylpolysiloxane, tristri-methylsiloxymethylsilane, caprylyl methicone, phenyl trimethicone, tetrakistrimethylsiloxysilane, methyl phenyl polysiloxane, methyl hexyl polysiloxane, methyl hydrogen polysiloxane, dimethyl siloxane•methylphenylsiloxane copolymer, etc., a cyclic organopolysiloxane such as octamethylcyclotetrasiloxane, decamethylcyclopentasiloxane, dodecamethylcyclohexasiloxane, tetramethyltetrahydrogen-cyclotetrasiloxane, tetramethyltetraphenylcyclotetra-siloxane, etc., silicone rubbers such as amino-modified organopolysiloxane, pyrrolidone-modified organopolysiloxane, pyrrolidone carboxylate-modified organopolysiloxane, gum dimethyl polysiloxane with high polymerization degree, gum aminomodified organopolysiloxane, and gum dimethylsiloxane/methylphenylsiloxane copolymer, etc., and a cyclic organopolysiloxane solution of silicone gum or rubber, trimethylsiloxysilicic acid, a cyclic siloxane solution of trimethylsiloxysilicic acid, a higher alkoxy-modified silicone such as stearoxysilicone, etc., a higher fatty acid-modified silicone, an alkyl-modified silicone, a long-chain alkyl-modified silicone, an amino acid-modified silicone, a fluorine-modified silicone, a silicone resin and a dissolved product of a silicone resin, etc.

As the fluorine-based oil, there may be exemplified by perfluoropolyether, perfluorodecalin, perfluorooctane, etc. A formulation amount of these oils may vary depending on the agent system, and is preferably in the range of 1 to 98% by mass based on the entire cosmetic.

In the cosmetic of the present invention, water can be also formulated depending on the purpose. A formulation amount thereof may vary depending on the formulation system, and is preferable in the range of 1 to 95% by mass based on the entire cosmetic.

In the cosmetic of the present invention, one kind or two or more kinds of a lower alcohol having 2 to 5 carbon atoms and a polyhydric alcohol having 2 to 10 carbon atoms may be used depending on the purpose. As the alcohol, there are a lower alcohol such as ethanol, isopropanol, etc., and a sugar alcohol such as sorbitol, maltose, etc., and a sterol such as cholesterol, sitosterol, phytosterol and lanosterol, etc., and a polyhydric alcohol such as butylene glycol, propylene glycol, dibutylene glycol, pentylene glycol, etc. As the formulation amount thereof, it is preferably in the range of 0.1 to 98% by mass based on the entire cosmetic.

In the cosmetic of the present invention, water-soluble or water-swellable polymers can be used depending on the purpose. For example, there are plant-based polymers such as gum arabic, tragacanth, galactan, carob gum, guar gum, karaya gum, carrageenan, pectin, agar, quince seed (marmelo), starch (rice, corn, potato, wheat etc.), algae colloid, trant gum, locust bean gum, etc., microorganism-based polymers such as xanthan gum, dextran, succinoglucan, pullulan, etc., animal-based polymers such as collagen, casein, albumin, gelatin, etc., starch-based polymers such as carboxymethyl starch, methylhydroxypropyl starch, etc., cellulose-based polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose and cellulose powder, alginic acid-based polymers such as sodium alginate, alginic acid propylene glycol ester, etc., vinyl-based polymers such as polyvinyl methyl ether, carboxy vinyl polymer, etc., polyoxyethylene-based polymers, polyoxyethylene polyoxypropylene copolymer-based polymers, acrylic-based polymers such as sodium polyacrylate, polyethyl acrylate, polyacrylamide, acryloyldimethyltaurine salt copolymer, etc., other synthetic water-soluble polymers such as polyethyleneimine and cationic polymer, etc., inorganic-based water-soluble polymers such as bentonite, magnesium aluminum silicate, montmorillonite, beidellite, nontronite, saponite, hectorite, silicic anhydride, etc.

Among them, one kind or two or more kinds of water-soluble thickening agent selected from plant-based polymers, microorganism-based polymers, animal-based polymers, starch-based polymers, cellulose-based polymers, alginic acid-based polymers, polyoxyethylene polyoxypropylene copolymer-based polymers, acrylic-based polymers, and inorganic-based water-soluble polymers are preferably used.

A formulation amount in the case of using a water-soluble or water-swellable polymer is preferably in the range of 0.1 to 25% by mass based on the entire cosmetic.

In the cosmetic of the present invention, one kind or two or more kinds of powder may be used depending on the purpose. As the powder, any of the materials can be used as long as it is used for the usual cosmetic, regardless of its shape (spherical, needle-like, plate-like, etc.) or particle diameter (fumed, fine particles, pigment grade, etc.), particulate structure (porous, nonporous, etc.), and there may be exemplified by powder, for example, selected from inorganic powder, organic powder, surfactant metal salt powder, colored pigment, pearl pigment, metal powder pigment, tar pigment, natural pigment, etc.

Specifically, as the inorganic powder, there may be exemplified by titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, magnesium aluminum silicate, calcium silicate, barium silicate, strontium silicate, metal tungstate, hydroxyapatite, vermiculite, Higilite, bentonite, montmorillonite, hectorite, zeolite, ceramic powder, dibasic calcium phosphate, alumina, aluminum hydroxide, boron nitride, boron nitride, silica, etc.

As the organic powder, there may be exemplified by polyamide powder, polyester powder, polyethylene powder, polypropylene powder, polystyrene powder, polyurethane, benzoguanamine powder, polymethylbenzoguanamine powder, tetrafluoroethylene powder, polymethyl methacrylate powder, cellulose, silk powder, Nylon powder, 12 Nylon, 6 Nylon, silicone powder, styrene•acrylic acid copolymer, divinylbenzene•styrene copolymer, vinyl resin, urea resin, phenol resin, fluorine resin, silicon resin, acrylic resin, melamine resin, epoxy resin, polycarbonate resin, microcrystalline fiber powder, starch powder, lauroyl lysine, etc.

As the surfactant metal salt powder (metallic soap), there may be exemplified by zinc stearate, aluminum stearate, calcium stearate, magnesium stearate, zinc myristate, magnesium myristate, zinc cetyl phosphate, calcium cetyl phosphate, zinc sodium cetyl phosphate, etc.

As the colored pigment, there may be exemplified by inorganic red pigments such as iron oxide, iron hydroxide and iron titanate, inorganic brown pigments such as γ-iron oxide, etc., inorganic yellow pigments such as yellow iron oxide, loess, etc., inorganic black pigments such as black iron oxide, carbon black, etc., inorganic violet pigments such as manganese violet, cobalt violet, etc., inorganic green pigments such as chromium hydroxide, chromium oxide, cobalt oxide, cobalt titanate, etc., inorganic blue pigments such as prussian blue, ultramarine blue, etc., those obtained by laking tar pigments, those obtained by laking natural dyes, and synthetic resin powders obtained by combining these powders, etc.

As the pearl pigment, there may be exemplified by titanium oxide-coated mica, titanium oxide-coated mica, bismuth oxychloride, titanium oxide-coated bismuth oxychloride, titanium oxide-coated talc, fish scale foil, titanium oxide-coated colored mica, etc.

As the metal powder pigment, there may be exemplified by aluminum powder, copper powder, stainless powder, etc.

As the tar pigment, there may be exemplified by Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, etc.

As the natural pigment, there may be exemplified by carminic acid, laccaic acid, carthamin, brazilin, crocin, etc.

As these powders, those in which powders are compounded, or those treated with general oil, silicone oil, a fluorine compound, a surfactant, etc., may be also used, and one kind or two or more kinds of those treated with a hydrolyzable silyl group or an alkyl group having a hydrogen atom directly bonded to a silicon atom, a linear and/or branched organopolysiloxane having a hydrolyzable silyl group or a hydrogen atom directly bonded to a silicon atom, a linear and/or branched organopolysiloxane having a hydrolyzable silyl group or a hydrogen atom directly bonded to a silicon atom and being co-modified by a long chain alkyl, a linear and/or branched organopolysiloxane having a hydrolyzable silyl group or a hydrogen atom directly bonded to a silicon atom and being co-modified by polyoxyalkylene, an acrylic-silicone-based copolymer having a hydrolyzable silyl group or a hydrogen atom directly bonded to a silicon atom, etc., may be also used depending on necessity.

In addition, a formulation amount of the powder is preferably in the range of 0.1 to 99% by mass based on the entire cosmetic. In particular, a formulation amount in the case of powdered solid cosmetic is preferably in the range of 80 to 99% by mass based on the entire cosmetic.

In the cosmetic of the present invention, one kind or two or more kinds of surfactants may be used depending on the purpose. As such a surfactant, there are anionic, cationic, nonionic and amphoteric active agents, but it is not particularly limited, and any material can be used as long as it is used in the usual cosmetic.

As the anionic surfactant, there may be exemplified by a fatty acid soap such as sodium stearate and triethanolamine palmitate, etc., an alkyl ether carboxylic acid and a salt thereof, a salt of a condensate of an amino acid and a fatty acid, an alkane sulfonate, an alkene sulfonate, a sulfonic acid salt of a fatty acid ester, a sulfonic acid salt of a fatty acid amide, a sulfonic acid salt of a formalin condensate, a sulfuric acid ester salt such as an alkyl sulfuric acid ester salt, a secondary higher alcohol sulfuric acid ester salt, an alkyl and allyl ether sulfuric acid ester salt, a sulfuric acid ester salt of a fatty acid ester, a sulfuric acid ester salt of a fatty acid alkylol amide, Turkey red oil, etc., an alkyl phosphate, an ether phosphate, an alkyl allyl ether phosphate, an amide phosphate, an N-acyl lactate, an N-acyl sarcosine salt, an N-acylamino acid-based active agent, etc.

As the cationic surfactant, there may be exemplified by an amine salt such as an alkylamine salt, a polyamine and an amino alcohol fatty acid derivative, etc., an alkyl quaternary ammonium salt, an aromatic quaternary ammonium salt, a pyridium salt, an imidazolium salt, etc.

As the nonionic surfactant, there may be exemplified by a sorbitan fatty acid ester, a glycerin fatty acid ester, a polyglycerin fatty acid ester, a propylene glycol fatty acid ester, a polyethylene glycol fatty acid ester, a sucrose fatty acid ester, a methyl glucoside fatty acid ester, an alkyl polyglucoside, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene propylene glycol fatty acid ester, a polyoxyethylene castor oil, a polyoxyethylene hardened castor oil, a polyoxyethylene phytostanol ether, a polyoxyethylene phytosterol ether, a polyoxyethylene cholestanol ether, a polyoxyethylene cholesteryl ether, a linear or branched polyoxyalkylene-modified organopolysiloxane, a linear or branched polyoxyalkylene•alkyl-co-modified organopolysiloxane, a linear or branched polyglycerin-modified organopolysiloxane, a linear or branched polyglycerin•alkyl-co-modified organopolysiloxane, an alkanol amide, a sugar ether, a sugar amide, etc.

As the amphoteric surfactant, there may be exemplified by betaine, phosphatidylcholine, aminocarboxylic acid salt, imidazoline derivative, amideamine type, etc. Among these surfactants, it is preferably a linear or branched organopolysiloxane having a polyoxyalkylene chain or a polyglycerin chain in the molecule, or further a linear or branched organopolysiloxane having a long chain alkyl group having 6 to 20 carbon atoms.

Also, in these surfactants, a content of a hydrophilic polyoxyalkylene group or a polyglycerin residue preferably occupies 10 to 70% by mass in the molecule, and a formulation amount thereof is preferably in the range of 0.1 to 20% by mass, particularly preferably 0.2 to 10% by mass based on the entire cosmetic.

The cosmetic of the present invention may contain a silicone resin selected from an acrylic silicone resin and a network silicone resin. The acrylic silicone resin is an acrylic/silicone graft or block copolymer. In addition, an acrylic silicone resin containing at least one kind selected from anionic groups such as a pyrrolidinyl group, a long chain alkyl group, a polyoxyalkylene group and a fluoroalkyl group, and a carboxyl group, etc., in the molecule may be also used.

The network silicone resin is selected from a resin composed of a $R^{1s}{}_3SiO_{0.5}$ unit and a $SiO_2$ unit, a resin composed of a $R^{1s}{}_3SiO_{0.5}$ unit, a $R^{1s}{}_3SiO$ unit and a $SiO_2$ unit, a resin composed of a $R^{1s}{}_3SiO_{0.5}$ unit and a $R^{1s}SiO_{1.5}$ unit, a resin composed of a $R^{1s}{}_3SiO_{0.5}$ unit, a $R^{1s}{}_2SiO$ unit and a $R^{1s}SiO_{1.5}$ unit, and a resin composed of a $R^{1s}{}_3SiO_{0.5}$ unit, a $R^{1s}{}_2SiO$ unit, a $R^{1s}SiO_{1.5}$ unit and a $SiO_2$ unit. Here, $R^{1s}$ represents an organic group. In addition, a network silicone containing at least one kind selected from a pyrrolidinyl group, a long chain alkyl group, a polyoxyalkylene group and a fluoroalkyl group, and an amino group in the molecule may be also used. A formulation amount in the case of using the silicone resin is preferably 0.1 to 20% by mass, more preferably 1 to 10% by mass based on the total mass of the cosmetic.

In the cosmetic of the present invention, a composition comprising one kind or two or more kinds of a crosslinking type organopolysiloxane and an oil agent (liquid oil) which is liquid at room temperature may be also used depending on the purpose. The crosslinking type organopolysiloxane is preferably swollen with respect to the liquid oil by containing it in an amount of its own weight or more of the liquid oil.

As the liquid oil, the liquid silicone oil, hydrocarbon oil, ester oil, natural animal and vegetable oil, semisynthetic oil, etc., and fluorine-based oil can be used and, for example, there may be exemplified by low kinematic viscosity silicone oil with 0.65 to 100.0 mm²/sec (25° C.), hydrocarbon oils such as liquid paraffin, squalane, isododecane, isohexadecane, etc., glyceride oils such as trioctanoin, etc., ester oils such as isotridecyl isononanoate, N-acyl glutamic acid ester, lauroyl sarcosinic acid ester, etc., and natural animal and vegetable oils such as macadamia nut oil, etc.

Also, a crosslinking agent of the crosslinking type organopolysiloxane is preferably a material having two or more vinylic reactive sites in the molecule, and, forming a crosslinked structure by reacting with a hydrogen atom directly bonded to a silicon atom. The material having two or more vinylic reactive sites in the molecule may be mentioned an organopolysiloxane having two or more vinyl groups in the molecule, a polyoxyalkylene having two or more allyl groups in the molecule, a polyglycerin having two or more allyl groups in the molecule, α,ω-alkenyldiene, etc. In addition, a crosslinking agent having at least one selected from the group consisting of a polyoxyalkylene group, a polyglycerin residue, a long chain alkyl group, an alkenyl group, an aryl group, and a fluoroalkyl group can be also used.

A formulation amount in the case of using the composition comprising the crosslinking type organopolysiloxane and the oil agent which is liquid at room temperature is preferably 0.1 to 80% by mass, more preferably 1 to 50% by mass based on the total mass of the cosmetic.

In the cosmetic of the present invention, a silicone-modified olefin wax obtained by subjecting an olefin wax having an unsaturated group obtained by reacting one kind or two or more kinds of α-olefins and a diene and an organohydrogen polysiloxane having one or more SiH bonds in one molecule to addition reaction may be contained depending on the purpose. As the α-olefin, those having 2 to 12 carbon atoms such as ethylene, propylene, 1-butene, 1-hexene, 4-methyl 1-pentene, etc., are preferable, and as the diene, butadiene, isoprene, 1,4-hexadiene, vinyl norbornene, ethylidene norbornene, dicyclopentadiene, etc., are preferable. As the organohydrogen polysiloxane having a SiH bond, those having a structure of a linear or a siloxane branched type, etc., can be used.

Further, to the cosmetic of the present invention, components to be used for usual cosmetics, oil-soluble gelling agent, antiperspirant, ultraviolet absorber, ultraviolet absorptive scattering agent, moisturizing agent, antimicrobial preservative, antimicrobial agent, perfume, salts, antioxidant, pH adjuster, chelating agent, refrigerant, anti-inflammatory agent, skin beautifying component (whitening agent, cell activator, rough skin ameliorating agent, blood circulation promoter, skin astringent, antiseborrheic drug, etc.), vitamins, amino acids, nucleic acids, hormones, inclusion compounds, solidifying agents for hair, etc., may be added.

As the oil-soluble gelling agent, there may be exemplified by a gelling agent selected from a metallic soap such as aluminum stearate, magnesium stearate, zinc myristate, etc., an amino acid derivative such as N-lauroyl-L-glutamic acid, α,γ-di-n-butylamine, etc., a dextrin ester of fatty acid such as dextrin ester of palmitic acid, dextrin ester of stearic acid, dextrin ester of 2-ethylhexanoic/palmitic acid, etc., a sucrose fatty acid ester such as sucrose palmitate, sucrose stearate, etc., a fructo-oligosaccharide fatty acid ester such as fructo-oligosaccharide stearate, fructo-oligosaccharide 2-ethylhexanoate, etc., a benzylidene derivative of sorbitol such as monobenzylidene sorbitol, dibenzylidene sorbitol, etc., organic-modified clay minerals such as dimethylbenzyldodecylammonium montmorillonite clay, dimethyldioctadecylammonium montmorillonite clay, etc.

As the antiperspirant, there may be exemplified by an antiperspirant selected from aluminum chlorohydrate, aluminum chloride, aluminum sesquichlorohydrate, zirconyl hydroxychloride, aluminum zirconium hydroxychloride, aluminum zirconium glycine complex, etc.

As the ultraviolet absorber, there may be exemplified by a benzoic acid-based ultraviolet absorber such as para-aminobenzoic acid, etc., an anthranilic acid-based ultraviolet absorber such as methyl anthranilate, etc., a salicylic acid-based ultraviolet absorber such as methyl salicylate, octyl salicylate, trimethylcyclohexylhexyl salicylate, etc., a cinnamic acid-based ultraviolet absorber such as octyl paramethoxycinnamate, etc., a benzophenone-based ultraviolet absorber such as 2,4-dihydroxybenzophenone, etc., an urocanic acid-based ultraviolet absorber such as ethyl urocanate, etc., a dibenzoylmethane-based ultraviolet absorber such as 4-t-butyl-4'-methoxy-dibenzoylmethane, etc., phenylbenzimidazole sulfonic acid, a triazine derivative, etc., and as the ultraviolet absorptive scattering agent, there may be exemplified by powder which absorbs or scatters ultraviolet rays such as fine particulate titanium oxide, fine particulate iron-containing titanium oxide, fine particulate zinc oxide, fine particulate cerium oxide and a complex thereof, etc., and a dispersion in which these powders which absorb and scatter ultraviolet rays are dispersed in oil in advance can be also used.

As the moisturizing agent, there are glycerin, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carboxylate, polyoxyethylene methyl glucoside, polyoxypropylene methyl glucoside, egg yolk lecithin, soybean lecithin, phosphatidylcholine, phosphatidylethanolamine, phosphadithyl serine, phosphatidyl glycerol, phosphatidylinositol, sphingophospholipid, etc.

As the antimicrobial preservative, there are paraoxybenzoic acid alkyl ester, benzoic acid, sodium benzoate, sorbic acid, potassium sorbate, phenoxyethanol, etc., and as the antimicrobial agent, there are benzoic acid, salicylic acid, carbolic acid, sorbic acid, paraoxybenzoic acid alkyl ester, parachlorometacresol, hexachlorophene, benzalkonium chloride, chlorhexidine chloride, trichlorocarbanilide, photosensitizer, phenoxyethanol, etc.

As the perfume, there may be exemplified by a natural perfume and a synthetic perfume. As the natural perfume, there may be exemplified by vegetable perfume separated from flowers, leaves, wood, pericarp, etc.; and animal perfume such as musk, civet, etc. As the synthetic perfume, there may be exemplified by a hydrocarbon such as monoterpene, etc.; an alcohol such as an aliphatic alcohol, an aromatic alcohol, etc.; an aldehyde such as terpene aldehyde, aromatic aldehyde, etc.; a ketone such as an alicyclic ketone, etc.; an ester such as a terpene-based ester, etc.; a lactone; a phenol; an oxide; a nitrogen-containing compound; an acetal, etc.

As the salts, there may be exemplified by an inorganic salt, an organic salt, an amine salt and an amino acid salt. As the inorganic salt, for example, there are a sodium salt, a potassium salt, a magnesium salt, a calcium salt, an aluminum salt, a zirconium salt, a zinc salt, etc., of an inorganic acid such as hydrochloric acid, sulfuric acid, carbonic acid, nitric acid, etc.; as the organic salt, for example, a salt of an organic acid such as acetic acid, dehydroacetic acid, citric acid, malic acid, succinic acid, ascorbic acid, stearic acid, etc.; and as the amine salt and the amino acid salt, for example, a salt of an amine such as triethanolamine, etc., and a salt of an amino acid such as glutamic acid, etc. In addition, as others, a salt of hyaluronic acid, chondroitin sulfuric acid, etc., aluminum zirconium glycine complex, etc., and further an acid-alkali neutralizing salt used in cosmetic prescription can be also used.

As the antioxidant, there may be exemplified by tocopherol, p-t-butylphenol, butylhydroxyanisole, dibutylhydroxytoluene, phytic acid, etc., as the pH adjuster, lactic acid, citric acid, glycolic acid, succinic acid, tartaric acid, dl-malic acid, potassium carbonate, sodium hydrogen carbonate, ammonium hydrogen carbonate, etc., as the chelating agent, alanine, sodium edetate, sodium polyphosphate, sodium metaphosphate, phosphoric acid, etc., as the refrigerant, L-menthol, camphor, etc., and as the anti-inflammatory agent, allantoin, glycyrrhizic acid and a salt thereof, glycyrrhetinic acid and stearyl glycyrrhetinate, tranexamic acid, azulene, etc.

As the skin beautifying component, there may be exemplified by a whitening agent such as placenta extract, arbutin, glutathione, saxifrage extract, etc., a cell activator or a rough skin ameliorating agent such as royal jelly, a photosensitizer, a cholesterol derivative, bovine blood extract, etc., a blood circulation promoter such as nonylic acid vanillylamide, benzyl nicotinate, β-butoxyethyl nicotinate, capsaicin, zingerone, cantharides tincture, ichthammol, caffeine, tannic acid, α-borneol, tocopherol nicotinate, inositol hexanicotinate, cyclandelate, cinnarizine, tolazoline, acetylcholine, verapamil, cepharanthin, γ-oryzanol, etc., a skin astringent such as zinc oxide, tannic acid, etc., and an antiseborrheic drug such as sulfur, thiantrol, etc.

As the vitamins, there are vitamin A such as vitamin A oil, retinol, retinol acetate, retinol palmitate, etc., vitamin B2 such as riboflavin, riboflavin butyrate, flavin adenine nucleotide, etc., vitamin B6 such as pyridoxine hydrochloride, pyridoxine dioctanoate, pyridoxine tripalmitate, etc., vitamin B such as vitamin B12 and a derivative thereof, vitamin B15 and a derivative thereof, etc., vitamin C such as L-ascorbic acid, L-ascorbic acid dipalmitate, L-ascorbic acid-2-sulfate sodium, L-ascorbic acid phosphate diester dipotassium, etc., vitamin D such as ergocalciferol, cholecalciferol, etc., vitamin E such as α-tocopherol, β-tocopherol, γ-tocopherol, dl-α-tocopherol acetate, dl-α-tocopherol nicotinate, dl-α-tocopherol succinate, etc., vitamin H, vitamin P, nicotinic acids such as nicotinic acid, benzyl nicotinate, nicotinic acid amide, etc., pantothenic acids such as calcium pantothenate, D-pantothenyl alcohol, pantothenyl ethyl ether, acetyl pantothenyl ethyl ether, etc., and biotin, etc.

As the amino acids, there may be exemplified by glycine, valine, leucine, isoleucine, serine, threonine, phenylalanine, arginine, lysine, aspartic acid, glutamic acid, cystine, cysteine, methionine, tryptophan, etc., as the nucleic acid, there may be exemplified by deoxyribonucleic acid, etc., and as the hormone, there may be exemplified by estradiol, ethenyl estradiol, etc.

As the inclusion compound, there may be exemplified by cyclodextrin, etc.

As the solidifying agents for hair, there may be exemplified by each of amphoteric, anionic, cationic, and nonionic polymer compound, and may be mentioned a polyvinylpyrrolidone-based polymer compound such as polyvinylpyrrolidone, a vinylpyrrolidone/vinyl acetate copolymer, etc., an acidic vinyl ether-based polymer compound such as a methyl vinyl ether/maleic anhydride alkyl half ester copolymer, etc., an acidic polyvinyl acetate-based polymer such as a vinyl acetate/crotonic acid copolymer, etc., an acidic acrylic-based polymer compound such as a (meth)acrylic acid/alkyl (meth)acrylate copolymer, a (meth)acrylic acid/alkyl (meth)acrylate/alkyl acrylamide copolymer, etc., an amphoteric acrylic-based polymer compound such as an N-methacryloylethyl-N,N-dimethylammonium•α-N-methylcarboxybetaine/alkyl (meth)acrylate copolymer, a hydroxypropyl (meth)acrylate/butylaminoethyl methacrylate/octylamide acrylate copolymer, etc. In addition, a naturally-derived polymer compound such as cellulose or a derivative thereof, keratin and collagen or a derivative thereof, etc., can be also suitably used.

In the present invention, the dosage form or form of the cosmetic is not particularly limited, and it may be aqueous, oily, water-in-oil type emulsion, oil-in-water type emulsion, nonaqueous emulsion, multi-emulsion such as W/O/W and O/W/O, etc., suspension, paste, or solid.

In the case where the cosmetic of the present invention further contains the powder, it is preferable that it is in a form either of liquid, paste, or solid in which the powder is dispersed, since handling is good.

The use of the cosmetic may also be arbitrary. There may be mentioned, for example, skin care cosmetics such as skin lotion, milky lotion, cream, cleansing, pack, oil liquid, massaging agent, beauty essence, beauty oil, hand cream, lip cream, wrinkle concealment, etc.; makeup cosmetics such as makeup base, concealer, white powder, powder foundation, liquid foundation, cream foundation, oil foundation, blusher, eye shadow, mascara, eyeliner, eyebrow, lipstick, etc.; hair cosmetics such as shampoo, rinse, treatment, setting agent, etc.; ultraviolet protective cosmetics such as sunscreen oil and sunscreen milky lotion, sunscreen cream, etc.; and other detergents, deodorants, antiperspirants, etc.

In particular, those which further contains water and in the form of an emulsion are suitable as makeup base, liquid foundation, sunscreen milky lotion, sunscreen cream, etc.

Those which further contains either of silicone oil, ester oil, glyceride oil, or a mixture thereof, and in the form of a nonaqueous emulsion are suitable as oil foundation, lipstick, etc.

EXAMPLES

In the following, the present invention will be explained more specifically by referring to Examples and Comparative Examples, but the present invention is not limited by the following Examples.

Example 1

In a reactor were charged 38.4 parts by mass of triglycerin diallyl ether represented by the following average formula (4), $$CH_2=CHCH_2-O-[C_3H_5(OH)O-]_3CH_2CH=CH_2 \quad (4)$$

242 parts by mass of both terminal-hydrogen polysiloxane represented by the following average formula (5),

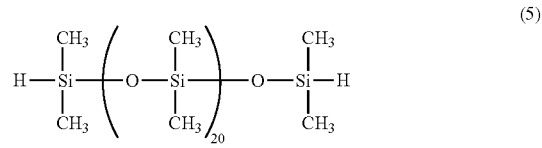

(5)

and 100 parts by mass of isopropyl alcohol, then, 0.12 parts by mass of a toluene solution containing 0.5% by mass of chloroplatinic acid was added to the mixture, and the resulting mixture was reacted under reflux for 3 hours, followed by adding 54.8 parts by mass of one-terminal vinyl-modified polysiloxane represented by the following average formula (6)

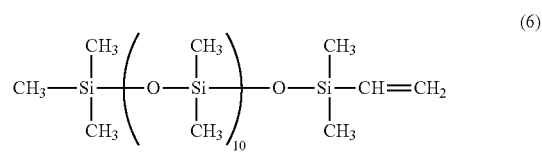

(6)

to react the mixture under reflux for 3 hours. The reaction product was heated under reduced pressure to distill off the solvent, whereby a polyglycerin group-containing organopolysiloxane represented by the following average formula (7) having a viscosity of 11,000 mPa·s and a number average molecular weight in terms of polystyrene of 18,300 was obtained.

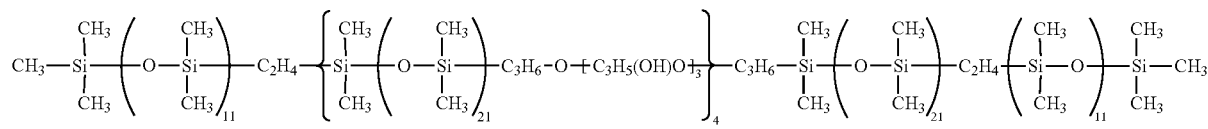
(7)

Example 2

In a reactor were charged 6.4 parts by mass of triglycerin diallyl ether represented by the following average formula (4),

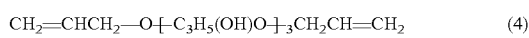
(4)

226 parts by mass of a both terminal-hydrogen polysiloxane represented by the following average formula (8),

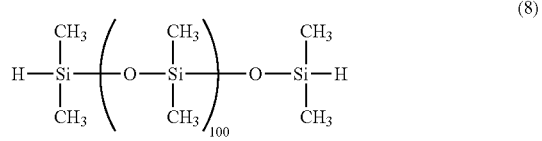
(8)

and 100 parts by mass of isopropyl alcohol, then, 0.15 parts by mass of a toluene solution containing 0.5% by mass of chloroplatinic acid was added to the mixture, and the resulting mixture was reacted under reflux for 3 hours, followed by adding 2.4 parts by mass of 1-octene, to react the mixture under reflux for 3 hours. The reaction product was heated under reduced pressure to distill off the solvent, whereby a polyglycerin group-containing organopolysiloxane represented by the following average formula (9) having a viscosity of 12,400 mPa·s and a number average molecular weight in terms of polystyrene of 35,000 was obtained.

124 parts by mass of a both terminal-hydrogen polysiloxane represented by the following average formula (11),

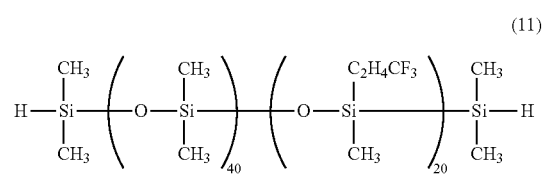
(11)

and 60 parts by mass of isopropyl alcohol, then, 0.03 parts by mass of a toluene solution containing 0.5% by mass of chloroplatinic acid was added to the mixture, and the resulting mixture was reacted under reflux for 3 hours, followed by adding 76.2 parts by mass of one-terminal vinyl-modified polysiloxane represented by the following average formula (12),

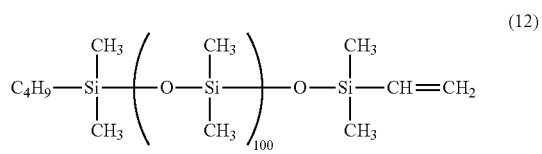
(12)

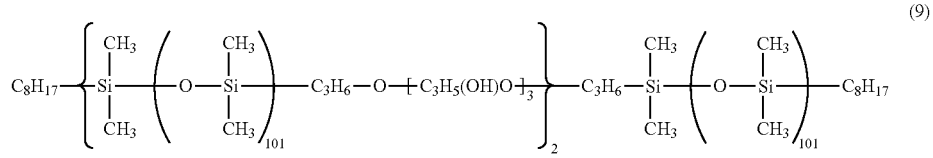
(9)

Example 3

In a reactor were charged 7.0 parts by mass of pentaglycerin diallyl ether represented by the following average formula (10),

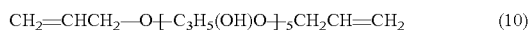
(10)

to react the mixture under reflux for 3 hours. The reaction product was heated under reduced pressure to distill off the solvent, whereby a polyglycerin group-containing organopolysiloxane represented by the following average formula (13) having a viscosity of 14,800 mPa·s, and a number average molecular weight in terms of polystyrene of 26,100 was obtained.

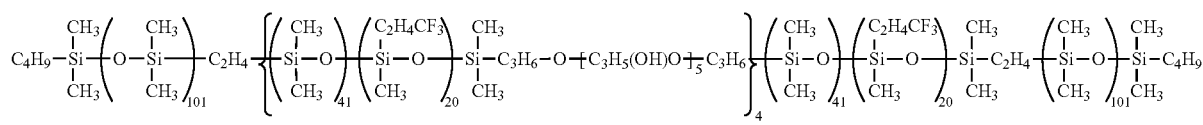
(13)

Example 4

In a reactor were charged 32.0 parts by mass of triglycerin diallyl ether resented by the following average formula (4), $$CH_2=CHCH_2-O+C_3H_5(OH)O+_3CH_2CH=CH_2 \quad (4)$$

224 parts by mass of both terminal-hydrogen polysiloxane represented by the following average formula (14),

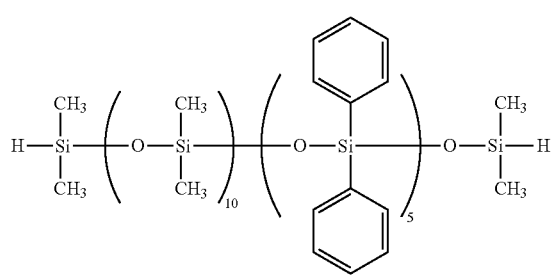

(14)

and 80 parts by mass of isopropyl alcohol, then, 0.15 parts by mass a toluene solution containing 0.5% by mass of chloroplatinic acid was added to the mixture, and the resulting mixture was reacted under reflux for 3 hours, followed by adding 9.0 parts by mass of 1-hexadecene to react the mixture under reflux for 3 hours. The reaction product was heated under reduced pressure to distill off the solvent, whereby a polyglycerin group-containing organopolysiloxane represented by the following average formula (15) having a viscosity of 16,500 mPa·s and a number average molecular weight in terms of polystyrene of 19,500 was obtained.

Example 5

In a reactor were charged 33.4 parts by mass of triglycerin diallyl monomethyl ether represented by the following average formula (16),

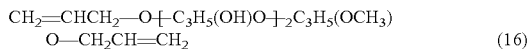

(16)

242 parts by mass of both terminal-hydrogen polysiloxane represented by the following average formula (5),

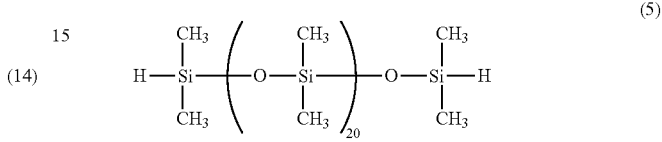

(5)

and 100 parts by mass of isopropyl alcohol, then, 0.12 parts by mass of a toluene solution containing 0.5% by mass of chloroplatinic acid was added to the mixture, and the resulting mixture was reacted under reflux for 3 hours, followed by adding 54.8 parts by mass of one-terminal vinyl-modified polysiloxane represented by the following average formula (6),

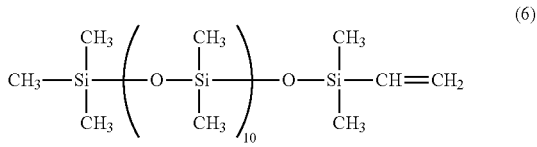

(6)

to react the mixture under reflux for 3 hours. The reaction product was heated under reduced pressure to distill off the solvent, whereby a polyglycerin group-containing organopolysiloxane represented by the following average formula (17) having a viscosity of 8,300 mPa·s and a number average molecular weight in terms of polystyrene of 14,100 was obtained.

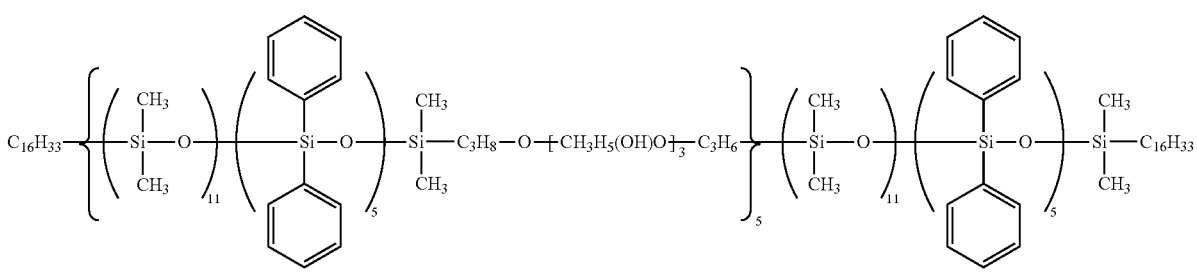

(15)

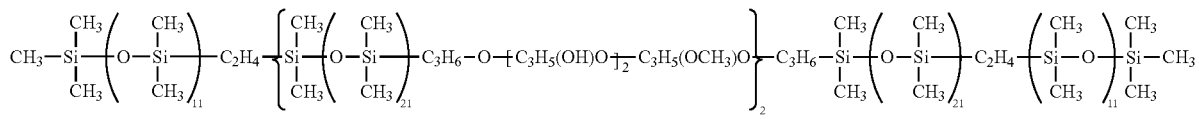
(17)

Example 6

In a reactor were charged 32.0 parts by mass of triglycerin diallyl ether represented by the following average formula (4),

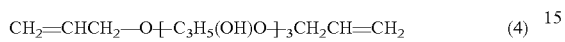
(4)

175 parts by mass of both terminal-hydrogen polysiloxane represented by the following average formula (18),

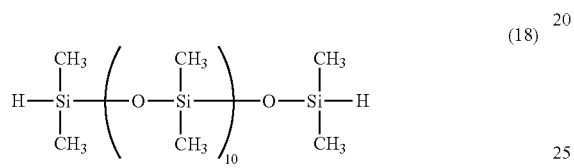
(18)

and 80 parts by mass of isopropyl alcohol, then, 0.15 parts by mass of a toluene solution containing 0.5% by mass of chloroplatinic acid was added to the mixture, and the resulting mixture was reacted under reflux for 3 hours, followed by adding 47.0 parts by mass of 1-hexadecene, to react the mixture under reflux for 3 hours. The reaction product was heated under reduced pressure to distill off the solvent, whereby a polyglycerin group-containing organopolysiloxane represented by the following average formula (19), having a viscosity of 320 mm$^2$/sec and a number average molecular weight in terms of polystyrene of 2,500 was obtained.

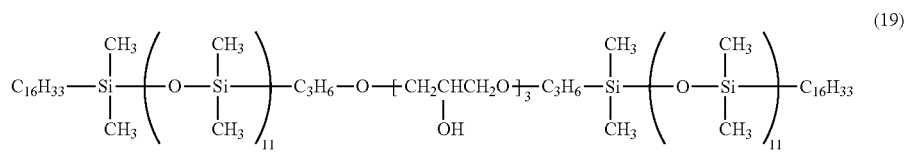
(19)

Examples 7 to 9, and Comparative Examples 1 to 2

A W/O emulsified product (formulation amount is shown by % by mass) having the composition shown in the following Table 1 was prepared by the following method.
(Manufacturing Method)
Components 1 to 6 were stirred and mixed at 1,500 rpm using a Disper mixer, then, Components 7 and 8 were gradually added to the mixture and the mixture was emulsified.
100 g of the obtained emulsified product was placed in a polypropylene container, allowed to stand at 50° C. for one month, thereafter the emulsified state and swelling of the container were observed with naked eyes, and the odor was evaluated by sensory evaluation according to the following criteria. The results are shown in Table 1.
(Evaluation criteria) Emulsified state: ○: no separation, Δ: slightly separated, x: separated to bilayer
Swelling of container: ○: no change, x there is swelling of container
Odor: ○: no offensive odor, x: there is specific odor

TABLE 1

| Component | Example 7 | Example 8 | Example 9 | Comparative example 1 | Comparative example 2 |
|---|---|---|---|---|---|
| 1 Dimethyl polysiloxane (6 mm²/sec) | 20 | 20 | 20 | 20 | 20 |
| 2 Organopolysiloxane of Example 1 | 2 | — | — | — | — |
| 3 Organopolysiloxane of Example 2 | — | 2 | — | — | — |
| 4 Organopolysiloxane of Example 3 | — | — | 2 | — | — |
| 5 Organopolysiloxane of following structural formula (Note 1) | — | — | — | 2 | — |
| 6 Organopolysiloxane of following structural formula (Note 2) | — | — | — | — | 2 |
| 7 1.3 Butylene glycol | 5 | 5 | 5 | 5 | 5 |
| 8 Purified water | 73 | 73 | 73 | 73 | 73 |
| Emulsion stability at 50° C./after one month | ○ | ○ | ○ | ○ | ○ |
| Swelling of vessel at 50° C./after one month | ○ | ○ | ○ | X | ○ |
| Odor at 50° C./after one month | ○ | ○ | ○ | ○ | X |

(Note 1)
Organopolysiloxane represented by the following formula described in Patent Document 13
Organopolysiloxane having Si—H groups at both terminals: reacted with a molar ratio of 5:4 of triglycerin diallyl ether (in the case of excess Si—H group)

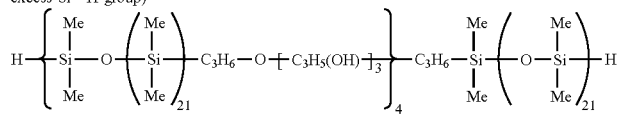

(Note 2)
Organopolysiloxane represented by the following formula described in Patent Document 13
Organopolysiloxane having Si—H groups at both terminals: reacted with a molar ratio of 4:5 of triglycerin diallyl ether (in the case of excess aliphatic unsaturated group)

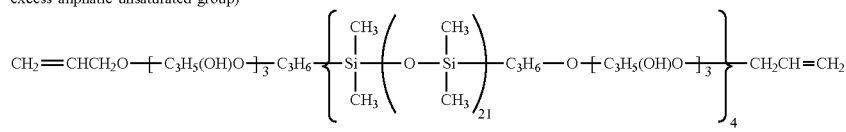

As shown in Table 1, the emulsified products of Examples 7, 8 and 9, and Comparative Examples 1 and 2 each maintained the initial emulsified state even after one month at 50° C., but in Comparative Example 1 in which a material remained the Si—H groups at the both terminals was used, the container was swelled and in Comparative Example 2 in which a material remained the aliphatic unsaturated group at the both terminals was used, a specific odor was generated.

Examples 10 to 12, and Comparative Examples 3 and 4

Using the organopolysiloxane obtained in Examples 1, 2 and 3, W/O type foundations were prepared with the compositions shown in the following Table 2, and stability with a lapse of time, swelling of the container, odor, and organoleptic evaluation were carried out. Similarly, as Comparative Examples 3 and 4, W/O type foundations were prepared with the compositions shown in the following Table 2.

The stability with a lapse of time, swelling of the container, and odor were evaluated according to the following criteria by observing the emulsified state with naked eyes after 100 g of the obtained foundation was placed in a polypropylene container and allowed to stand at 50° C. for one month.

(Evaluation criteria) Emulsified state: ○: no separation, Δ: slightly separated, x: separated to bilayer Swelling of container: ○: no change, x there is swelling of container Odor: ○: no offensive odor, x: there is specific odor

TABLE 2

| | Components | Formulation (parts by mass) | | | | |
|---|---|---|---|---|---|---|
| | | Example 10 | Example 11 | Example 12 | Comparative example 3 | Comparative example 4 |
| 1 | Decamethylcyclopentasiloxane | 45.0 | ← | — | ← | ← |
| 2 | Dimethylpolysiloxane | 5.0 | ← | — | ← | ← |
| 3 | Organopolysiloxane of Example 1 | 2.0 | — | — | — | — |
| 4 | Organopolysiloxane of Example 2 | — | 2.0 | — | — | — |
| 5 | Organopolysiloxane of Example 3 | — | — | 2.0 | — | — |
| 6 | Organopolysiloxane (Note 1) | — | — | — | 2.0 | — |
| 7 | Organopolysiloxane (Note 2) | — | — | — | — | 2.0 |
| 8 | Octadecyldimethylbenzyl ammonium salt-modified montmorillonite | 4.0 | ← | ← | ← | ← |
| 9 | Hydrophobic-treatment titanium oxide (Note 3) | 10.0 | ← | ← | ← | ← |

TABLE 2-continued

| | Components | Example 10 | Example 11 | Example 12 | Comparative example 3 | Comparative example 4 |
|---|---|---|---|---|---|---|
| | | Formulation (parts by mass) | | | | |
| 10 | Hydrophobic-treatment talc (Note 3) | 6.0 | ← | ← | ← | ← |
| 11 | Hydrophobic-treatment mica (Note 3) | 6.0 | ← | ← | ← | ← |
| 12 | Hydrophobic-treatment red iron oxide (Note 3) | 1.6 | ← | ← | ← | ← |
| 13 | Hydrophobic-treatment yellow iron oxide (Note 3) | 0.7 | ← | ← | ← | ← |
| 14 | Hydrophobic-treatment black iron oxide (Note 3) | 0.2 | ← | ← | ← | ← |
| 15 | Dipropylene glycol | 5.0 | ← | ← | ← | ← |
| 16 | Paraoxybenzoic acid methyl ester | 0.3 | ← | ← | ← | ← |
| 17 | Perfume | Suitable amount | ← | ← | ← | ← |
| 18 | Water | Remainder | ← | ← | ← | ← |
| | Emulsion stability at 50° C./after one month | ○ | ○ | ○ | Δ | Δ |
| | Swelling of vessel at 50° C./after one month | ○ | ○ | ○ | x | ○ |
| | Odor at 50° C./after one month | ○ | ○ | ○ | ○ | x |

(Note 1) and (Note 2) are the same as mentioned above
(Note 3)
Hydrophobic-treatment; After adding 2% of methylhydrogenpolysiloxane to the powder, heat treated
In Table 2, "←" means the same formulation amount as in Example 10.

(Manufacturing Method)

A: Components 1 to 8 were heated and mixed, and Components 9 to 14 were added to make it homogeneous.
B: Components 15, 16 and 18 were heated and dissolved.
C: Under stirring, B was gradually added to A to emulsify the mixture, then the mixture was cooled and Component 17 was added thereto to obtain a foundation.

The foundations obtained in Examples 10 to 12, and Comparative Examples 3 and 4 were subjected to a use test by special panels of 50 female workers and evaluated for the degree of usability, the degree of uniformity of color tone, and the degree of cosmetic durability according to the following criteria. The results are shown in Table 3.

[Evaluation Criteria]
5 points: Very good
4 points: Good
3 points: Normal
2 points: Slightly poor
1 point: Bad For each evaluation item, the average of the evaluation points of all the panels was taken. The meaning of each symbol in Table 3 is as follows.

The obtained average point is 4.5 points or more
⊚

The obtained average point is 3.5 points or more and less than 4.5 points
○

The obtained average point is 2.5 points or more and less than 3.5 points
Δ

The obtained average point is 1.5 points or more and less than 2.5 points
x

The obtained average point is less than 1.5 points
xx

TABLE 3

| | Example 10 | Example 11 | Example 12 | Comparative example 3 | Comparative example 4 |
|---|---|---|---|---|---|
| Degree of usability | ○ | ⊚ | ○ | ○ | ○ |
| Uniformity of color tone | ⊚ | ⊚ | ⊚ | Δ | Δ |
| Degree of cosmetic durability | ⊚ | ○ | ⊚ | Δ | ○ |

As shown in Table 2, the foundations of Comparative Example 3 in which a material remained Si—H groups at the both terminals was used and of Comparative Example 4 in which a material remained aliphatic unsaturated groups at the both terminals was used became worse in emulsification stability by mixing with various kinds of pigments, and in Comparative Example 3, swelling of the container was observed, and in Comparative Example 4, an offensive odor occurred.

Also, as shown in Table 3, the foundations of Comparative Examples 3 and 4 had good usability at the time of coating, and with regard to Comparative Example 4, cosmetic durability was also good, but the foundations of Comparative Examples 3 and 4 had poor pigment dispersibility so that the color tone was not uniform. To the contrary, the foundations of Examples 10 to 12 were good in usability and had good pigment dispersibility, so that the color tone was uniform, the affinity with the skin was excellent, and the cosmetic durability was also good.

In the following Examples, stability with a lapse of time was confirmed by no changes in appearance after leaving the cosmetic in a sealed container at 50° C. for 1 month.

Example 13: Eyeliner

TABLE 4

| | (Components) | (% by mass) |
|---|---|---|
| 1 | Octamethylcyclotetrasiloxane | Remainder |
| 2 | Organopolysiloxane of Example 4 | 3.0 |
| 3 | Silicone resin (Note 1) | 15.0 |
| 4 | Dioctadecyldimethyl ammonium salt-modified montmorillonite | 3.0 |
| 5 | Silicone-treated black iron oxide (Note 2) | 10.0 |
| 6 | 1,3-Butylene glycol | 5.0 |
| 7 | Sodium dehydroacetate | Suitable amount |

TABLE 4-continued

| | (Components) | (% by mass) |
|---|---|---|
| 8 | Antiseptic | Suitable amount |
| 9 | Perfume | Suitable amount |
| 10 | Purified water | 10.0 |

(Note 1)
Silicone resin: 50%-D5 solution of silicone network compound with a [Me$_3$SiO$_{1/2}$]/[SiO$_2$] ratio of 0.8
(Note 2)
Silicone-treated black iron oxide; a material in which 2% by mass of methylhydrogenpolysiloxane was added to the mass of black iron oxide, followed by heat-treatment at 150° C.

(Manufacturing Method)
A: Components 1 to 4 were mixed, and Component 5 was added to the mixture to uniformly mix and disperse.
B: Components 6 to 8 and 10 were mixed.
C: The mixture obtained in B was gradually added to the dispersion obtained in A to emulsify the mixture, then, Component 9 was added to obtain an eyeliner.

The eyeliner thus obtained was lightly spreadable and easy to draw, and had no stickiness and no change due to temperature or with a lapse of time, and cosmetic durability was very good.

Example 14: Suntan Cream

TABLE 5

| | (Components) | (% by mass) |
|---|---|---|
| 1 | Decamethylcyclopentasiloxane | 15.0 |
| 2 | Dimethylpolysiloxane (100 mm$^2$/sec) | 5.0 |
| 3 | Silicone wax | 0.5 |
| 4 | Organopolysiloxane of Example 5 | 6.0 |
| 5 | Palmitic acid | 0.2 |
| 6 | Dimethyloctyl paraaminobenzoic acid | 0.5 |
| 7 | 4-t-Butyl-4'-methoxy-dibenzoylmethane | 0.5 |
| 8 | Kaolin | 0.5 |
| 9 | Red iron oxide | 0.2 |
| 10 | Yellow iron oxide | 0.3 |
| 11 | Black iron oxide | 0.1 |
| 12 | Titanium oxide-coated mica | 1.0 |
| 13 | Sodium L-glutamate | 3.0 |
| 14 | 1,3-Butylene glycol | 5.0 |
| 15 | Dioctadecyldimethyl ammonium chloride | 0.1 |
| 16 | Antioxidant | Suitable amount |
| 17 | Antiseptic | Suitable amount |
| 18 | Perfume | Suitable amount |
| 19 | Purified water | Remainder |

(Manufacturing Method)
A: Components 1 to 7 and 16 to 17 were heated and dissolved.
B: After heating and stirring a part of Components 15 and 19, Components 8 to 12 were added and the mixture was subjected to dispersion treatment.
C: The remainder of Components 13 to 14 and 19 were dissolved, and mixed with the dispersion obtained in B.
D: Under stirring, the dispersion obtained in C was gradually added to the mixture obtained in A to emulsify the mixture, then the mixture was cooled and Component 18 was added thereto to obtain a suntan cream.

The suntan cream thus obtained had fine texture, light spreadability, no stickiness, freshness, fresh feeling of usage, and no change with a lapse of time. Moreover, it had good cosmetic durability.

Example 15: Cream

TABLE 6

| | (Components) | (% by mass) |
|---|---|---|
| 1 | Decamethylcyclopentasiloxane | 20.0 |
| 2 | Glyceryl trioctanoate | 10.0 |
| 3 | Organopolysiloxane of Example 1 | 4.0 |
| 4 | Phenyldimethylstearyl ammonium chloride | 1.0 |
| 5 | Dipropylene glycol | 10.0 |
| 6 | Maltitol | 10.0 |
| 7 | Saponite | 1.5 |
| 8 | Antiseptic | Suitable amount |
| 9 | Perfume | Suitable amount |
| 10 | Purified water | Reminder |

(Manufacturing Method)
A: Components 1 to 4 and 8 were heated and mixed.
B: Components 5 to 7 and 10 were heated and dissolved.
C: Under stirring, the solution obtained in B was gradually added to the mixture obtained in A to emulsify the mixture, then the mixture was cooled and Component 9 was added thereto to obtain a cream.

The cream thus obtained was lightly spreadable, free from stickiness and greasiness, fresh, and giving a refreshing feeling of usage, and had no change with a lapse of time.

Example 16: Sunscreen Cream

TABLE 7

| | (Components) | (% by mass) |
|---|---|---|
| 1 | Decamethylcyclopentasiloxane | 20.0 |
| 2 | Liquid paraffin | 10.0 |
| 3 | Organopolysiloxane of Example 2 | 4.0 |
| 4 | 4-t-Butyl-4'-methoxydibenzoylmethane | 7.0 |
| 5 | Distearyldimethyl ammonium chloride | 0.8 |
| 6 | Vitamin E acetate | 0.1 |
| 7 | Ethanol | 1.0 |
| 8 | Aluminum magnesium silicate | 1.2 |
| 9 | Antiseptic | Suitable amount |
| 10 | Perfume | Suitable amount |
| 11 | Purified water | Reminder |

(Manufacturing Method)
A: Components 1 to 6 and 9 were heated and mixed.
B: Components 7 to 8 and 11 were heated, and dispersed and mixed so as to be uniform.
C: Under stirring, the dispersion obtained in B was gradually added to the mixture obtained in A to emulsify the mixture, then the mixture was cooled and Component 10 was added thereto to obtain a sunscreen cream.

The sunscreen cream thus obtained was fine in texture and light in spreadability, and had no change with a lapse of time. Also, because there was no stickiness, sand did not stick at all and usability was very good. Further, since cosmetic durability was also good, the effect of preventing ultraviolet rays has been sustained.

Example 17: Eye Shadow

TABLE 8

| | (Components) | (% by mass) |
|---|---|---|
| 1 | Decamethylcyclopentasiloxane | 15.0 |
| 2 | Dimethylpolysiloxane (6 mm$^2$/sec) | 10.0 |
| 3 | Organopolysiloxane of Example 2 | 2.0 |
| 4 | PEG (10) lauryl ether | 0.5 |
| 5 | Silicone-treatment chromium oxide (Note 1) | 6.2 |
| 6 | Silicone-treatment ultramarine blue (Note 1) | 4.0 |
| 7 | Silicone-treatment titanium-coated mica (Note 1) | 6.0 |
| 8 | Sodium chloride | 2.0 |
| 9 | Propylene glycol | 8.0 |
| 10 | Antiseptic | Suitable amount |
| 11 | Perfume | Suitable amount |
| 12 | Purified water | Reminder |

(Note 1)
Silicone-treatment; A material in which after adding 3% by mass of methylhydrogen polysiloxane based on the powder mass, heat treated at 150° C.

(Manufacturing Method)
A: Components 1 to 4 were mixed, and Components 5 to 7 were added to the mixture and dispersed so as to be uniform.
B: Components 8 to 10 and 12 were uniformly dissolved.
C: Under stirring, the solution obtained in B was gradually added to the dispersed material obtained in A to emulsify the mixture, and Component 11 was added to the mixture to obtain an eye shadow.

It was found that the eye shadow thus obtained was light in spreadability, did not have oiliness and powderiness, was fresh, gave a refreshing feeling of usage, had good water resistance, water repellency and perspiration resistance, good durability, less makeup deterioration, and no change due to temperature or with a lapse of time, and was also excellent in stability.

Example 18: Lip Cream

TABLE 9

| | (Components) | (% by mass) |
|---|---|---|
| 1 | Decamethylcyclopentasiloxane | 40.0 |
| 2 | Isoparaffin (boiling point 155° C.) | 10.0 |
| 3 | Squalane | 10.0 |
| 4 | Lanolin | 2.0 |
| 5 | Trimethylsiloxysilicate | 3.0 |
| 6 | Microcrystalline wax | 3.0 |
| 7 | Organopolysiloxane of Example 5 | 3.0 |
| 8 | Lauroyl glutamic acid dibutylamide | 5.0 |
| 9 | Sodium lactate | 0.3 |
| 10 | Sodium L-glutamate | 0.3 |
| 11 | Sodium hyaluronate | 0.1 |
| 12 | Sorbitol | 0.5 |
| 13 | Glycerin | 5.0 |
| 14 | Red No. 202 | Suitable amount |
| 15 | Menthol | Suitable amount |
| 16 | Antiseptic | Suitable amount |
| 17 | Perfume | Suitable amount |
| 18 | Purified water | Remainder |

(Manufacturing Method)
A: Components 1 to 8 were heated and mixed.
B: Components 9 to 16 and 18 were heated and dissolved.
C: Under stirring, the solution obtained in B was gradually added to the mixture obtained in A to emulsify the mixture, Component 17 was added to the mixture and the mixture was filled in a capsule to obtain a lip cream.

The solid state water-in-oil type lip cream thus obtained was light in spreadability, free from stickiness and greasiness, moist and fresh, and giving a refreshing feeling of use, and had no change with a lapse of time, and the applied lip cream had good durability.

Example 19: Liquid Emulsified Foundation

TABLE 10

| | (Components) | (% by mass) |
|---|---|---|
| 1 | Dimethylpolysiloxane (6 mm$^2$/sec) | 5.0 |
| 2 | Decamethylcyclopentasiloxane | 15.0 |
| 3 | Squalane | 4.0 |
| 4 | Neopentyl glycol dioctanoate | 3.0 |
| 5 | Isostearic/myristic diglycerides | 2.0 |
| 6 | α-Monoisostearyl glyceryl ether | 1.0 |
| 7 | Organopolysiloxane of Example 4 | 1.0 |
| 8 | Distearic acid aluminum salt | 0.2 |
| 9 | Hydrophobic-treatment titanium oxide (Note 1) | 5.0 |
| 10 | Hydrophobic-treatment celicite (Note 1) | 2.0 |
| 11 | Hydrophobic-treatment talc (Note 1) | 3.0 |
| 12 | Hydrophobic-treatment red iron oxide (Note 1) | 0.4 |
| 13 | Hydrophobic-treatment yellow iron oxide (Note 1) | 0.7 |
| 14 | Hydrophobic-treatment black iron oxide (Note 1) | 0.1 |
| 15 | Magnesium sulfate | 0.7 |
| 16 | Glycerin | 3.0 |
| 17 | Antiseptic | Suitable amount |
| 18 | Perfume | Suitable amount |
| 19 | Purified water | Remainder |

(Note 1)
Hydrophobic-treatment powder; Materials treated with 2% by mass of stearic acid based on the mass of the powder (Manufacturing Method)
A: Components 1 to 8 were heated and mixed, and Components 9 to 14 were added to make the mixture homogeneous.
B: Components 15 to 17 and 19 were heated and dissolved.
C: Under stirring, the solution obtained in B was gradually added to the mixture obtained in A to emulsify the mixture, then the mixture was cooled and Component 18 was added thereto to obtain a liquid state emulsified foundation.

The liquid state emulsified foundation thus obtained had low viscosity and fine texture, was light in spreadability, free from stickiness and greasiness, moist and fresh, and giving a refreshing feeling of use, and had no change with a lapse of time. It was also good in durability of the cosmetic on the skin.

Example 20: Transparent Gel Cosmetic

TABLE 11

| | (Components) | (% by mass) |
|---|---|---|
| 1 | Decamethylcyclopentasiloxane | 10.0 |
| 2 | Organopolysiloxane of Example 2 | 10.0 |
| 3 | 1,3-Butylene glycol | 10.0 |
| 4 | Polyethylene glycol 400 | 9.0 |
| 5 | 2-Hydroxyoctanoic acid | 1.0 |
| 6 | Sorbitol (70% aqueous solution) | 10.0 |
| 7 | Citric acid | Suitable amount |
| 8 | Sodium citrate | Suitable amount |
| 9 | Antiseptic | Suitable amount |
| 10 | Perfume | Suitable amount |
| 11 | Purified water | Reminder |

(Manufacturing Method)
A: Components 3 to 11 were uniformly dissolved.
B: Components 1 to 2 were mixed and made uniform.
C: Under stirring, the solution obtained in A was gradually added to the mixture obtained in B and the mixture was emulsified to obtain a transparent gel cosmetic.

The transparent gel cosmetic thus obtained was light in spreadability, free from stickiness and greasiness, moist and fresh, giving a refreshing feeling of use, and easy to fit in the skin, and had no change with a lapse of time.

Example 21: Sunscreen Cosmetic Lotion

TABLE 12

| | (Components) | (% by mass) |
|---|---|---|
| 1 | Decamethylcyclopentasiloxane | 14.0 |
| 2 | Organopolysiloxane of Example 3 | 10.0 |
| 3 | Squalane | 1.5 |
| 4 | Octyl paramethoxycinnamate | 3.0 |
| 5 | Hydrophobic-treatment ultrafine particle titanium oxide (Note 1) | 2.0 |
| 6 | 1,3-Butylene glycol | 10.0 |
| 7 | Sodium chloride | 2.0 |
| 8 | L-proline | 0.1 |
| 9 | 2-Hydroxyoctanoic acid | 1.0 |
| 10 | 2-Hydroxypropanoic acid | 5.0 |
| 11 | Sodium hydroxide | Suitable amount |
| 12 | Antiseptic | Suitable amount |
| 13 | Perfume | Suitable amount |
| 14 | Purified water | Reminder |

(Note 1)
Hydrophobic-treatment ultrafine particle titanium oxide; Titanium TTO-V-4 (available from Ishihara Sangyo Kaisha, Ltd.)

(Manufacturing Method)
A: Components 6 to 14 were dissolved so as to be uniform.
B: Components 1 to 4 were mixed and Component 5 was added to make the mixture homogeneous.
C: Under stirring, B was gradually added to A and the mixture was emulsified to obtain a sunscreen cosmetic lotion.

The sunscreen cosmetic lotion thus obtained was light in spreadability, free from stickiness and greasiness, moist and fresh, giving a refreshing feeling of use and easy to fit in the skin, and had no change with a lapse of time. In addition, it was also excellent in sunscreen effect.

Example 22: Milky Lotion

TABLE 13

| | (Components) | (% by mass) |
|---|---|---|
| 1 | Decamethylcyclopentasiloxane | 18.0 |
| 2 | Dimethylpolysiloxane (6 mm$^2$/sec) | 6.0 |
| 3 | Squalane | 5.0 |
| 4 | Neopentyl glycol dioctanoate | 3.0 |
| 5 | α-Monooleyl glyceryl ether | 1.0 |
| 6 | Organopolysiloxane of Example 3 | 2.0 |
| 7 | Distearyl acid aluminum salt | 0.2 |
| 8 | Magnesium sulfate | 0.7 |
| 9 | Glycerin | 5.0 |
| 10 | Antiseptic | Suitable amount |
| 11 | Perfume | Suitable amount |
| 12 | Purified water | Reminder |

(Manufacturing Method)
A: Components 1 to 7 were heated and mixed.
B: Components 8 to 10 and 12 were heated and dissolved.
C: Under stirring, the solution obtained in B was gradually added to the mixture obtained in A to emulsify the mixture, then the mixture was cooled and Component 11 was added thereto to obtain a milky lotion.

The milky lotion thus obtained had low viscosity and fine texture, was light in spreadability, free from stickiness and greasiness, moist and fresh, and giving a refreshing feeling of use, and had no change with a lapse of time. Further, it was also good in durability of the cosmetic on the skin.

Example 23: Sunscreen Cream

TABLE 14

| | (Components) | (% by mass) |
|---|---|---|
| 1 | Decamethylcyclopentasiloxane | 18.0 |
| 2 | Methylphenylpolysiloxane | 2.0 |
| 3 | Liquid paraffin | 1.5 |
| 4 | Organopolysiloxane of Example 4 | 4.0 |
| 5 | Octyl paramethoxycinnamate | 5.0 |
| 6 | 1,3-Butylene glycol | 4.0 |
| 7 | Sodium chloride | 1.0 |
| 8 | Antiseptic | Suitable amount |
| 9 | Perfume | Suitable amount |
| 10 | Purified water | Reminder |

(Manufacturing Method)
A: Components 1 to 5 were heated and mixed.
B: Components 6 to 8 and 10 were heated and dissolved.
C: Under stirring, the solution obtained in B was gradually added to the mixture obtained in A to emulsify the mixture, then the mixture was cooled and Component 9 was added thereto to obtain a sunscreen cream.

The sunscreen cream thus obtained was fine in texture, light in spreadability, moist and fresh, and free from greasiness and stickiness, and had no change with a lapse of time. In addition, the applied cream was excellent in water resistance and perspiration resistance, and had good cosmetic durability, and UV protection effect thereof was also continued.

Example 24: Liquid Foundation

TABLE 15

| | (Components) | (% by mass) |
|---|---|---|
| 1 | Decamethylcyclopentasiloxane | 16.0 |
| 2 | Dimethylpolysiloxane (6 mm²/sec) | 8.0 |
| 3 | Octyl paramethoxycinnamate | 3.0 |
| 4 | 12-Hydroxystearic acid | 1.0 |
| 5 | Fluorine-modified silicone (Note 1) | 15.0 |
| 6 | Organopolysiloxane of Example 1 | 5.0 |
| 7 | Spherical silicone resin powder (Note 2) | 3.0 |
| 8 | Fluorine compound-treatment fine particulate titanium oxide (Note 3) | 8.0 |
| 9 | Fluorine compound-treatment mica titanium (Note 3) | 1.0 |
| 10 | Fluorine compound-treatment titanium oxide (Note 3) | 5.0 |
| 11 | Fluorine compound-treatment red iron oxide (Note 3) | 0.9 |
| 12 | Fluorine compound-treatment yellow iron oxide (Note 3) | 2.0 |
| 13 | Fluorine compound-treatment black iron oxide (Note 3) | 1.0 |
| 14 | Ethanol | 15.0 |
| 15 | Glycerin | 3.0 |
| 16 | Magnesium sulfate | 1.0 |
| 17 | Antiseptic | Suitable amount |
| 18 | Perfume | Suitable amount |
| 19 | Purified water | Reminder |

(Note 1)
Fluorine-modified silicone; FL-100 (available from Shin-Etsu Chemical Co., Ltd.)
(Note 2)
Spherical silicone resin powder; KMP590 (available from Shin-Etsu Chemical Co., Ltd.)
(Note 3)
Fluorine compound-treatment; a material coated with 5% by perfluoroalkylethylphosphoric acid diethanolamine salt (Manufacturing Method)
A: Components 7 to 13 were uniformly mixed.
B: Components 1 to 6 were heated at 70° C. and mixed, and the mixture obtained in A was added thereto and dispersed and mixed so as to be uniform.
C: Components 14 to 17 and 19 were warmed to 40° C. to obtain a solution, which was gradually added to the dispersion obtained in B to emulsify the mixture, and the mixture was cooled and Component 18 was added thereto to obtain a liquid foundation.

The liquid foundation thus obtained had no stickiness, was light in spreadability, and yet gave a refreshing feeling. Also, there was no change with a lapse of time.

Example 25: Milky Lotion

TABLE 16

| | (Components) | (% by mass) |
|---|---|---|
| 1 | Decamethylcyclopentasiloxane | 15.0 |
| 2 | Methylphenylpolysiloxane | 5.0 |
| 3 | Squalene | 5.0 |
| 4 | Pentaerythrityl tetra-2-ethylhexanoate | 5.0 |
| 5 | Organopolysiloxane of Example 5 | 3.0 |
| 6 | Organopolysiloxane elastomer spherical powder (Note 1) | 2.0 |
| 7 | Hydrophobic silica (Note 2) | 0.5 |
| 8 | Magnesium ascorbyl phosphate | 1.0 |
| 9 | Sodium chloride | 1.0 |
| 10 | Polyethylene glycol 11000 | 1.0 |
| 11 | Propylene glycol | 8.0 |
| 12 | Antiseptic | Suitable amount |
| 13 | Perfume | Suitable amount |
| 14 | Purified water | Reminder |

(Note 1)
Organopolysiloxane elastomer spherical powder; KMP594 (available from Shin-Etsu Chemical Co., Ltd.)
(Note 2)
Hydrophobic silica; Aerosil R972 (available from Nippon Aerosil Co., Ltd.)

(Manufacturing Method)
A: Components 1 to 5 were uniformly mixed, and Components 6 to 7 were added thereto and dispersed so as to be uniform.
B: Components 8 to 10 were added to Component 14 to dissolve the mixture, and a material in which Components 11 and 12 had been mixed was further added thereto.
C: The mixture obtained in B was gradually added to the dispersion obtained in A, and then, the mixture was emulsified and cooled, and Component 13 was added thereto to obtain a milky lotion.

The milky lotion thus obtained was light in spreadability, had dry touch and no stickiness, and had no change with a lapse of time.

Example 26: Moisturizing Cream

TABLE 17

| | (Components) | (% by mass) |
|---|---|---|
| 1 | Decamethylcyclopentasiloxane | 10.0 |
| 2 | Methylphenylpolysiloxane | 3.0 |
| 3 | Liquid paraffin | 5.0 |
| 4 | Pentaerythrityl tetra-2-ethylhexanoate | 3.0 |
| 5 | Cetyl 2-ethylhexanoate | 5.0 |
| 6 | Organopolysiloxane of Example 3 | 1.0 |
| 7 | Organopolysiloxane elastomer spherical powder (Note 1) | 2.5 |
| 8 | Hydrophobic silica (Note 2) | 2.0 |
| 9 | Zinc stearate | 2.0 |
| 10 | Vitamin E acetate | 3.0 |
| 11 | Polyethylene glycol 400 | 1.0 |
| 12 | Sodium lactate | 1.0 |
| 13 | 1,3-Butylene glycol | 5.0 |
| 14 | Antiseptic | Suitable amount |
| 15 | Perfume | Suitable amount |
| 16 | Purified water | Reminder |

(Note 1)
Organopolysiloxane elastomer spherical powder; KMP594 (available from Shin-Etsu Chemical Co., Ltd.)
(Note 2)
Hydrophobic silica; Aerosil R972 (available from Nippon Aerosil Co., Ltd.)

(Manufacturing Method)
A: Components 1 to 6 and 9 to 10 were uniformly mixed, and Components 7 to 8 were added to the mixture to disperse them uniformly.
B: Components 11 to 14 and 16 were added and dissolved.
C: The solution obtained in B was gradually added to the mixture obtained in A to emulsify the mixture, then the mixture was cooled and Component 15 was added thereto to obtain a moisturizing cream.

The moisturizing cream thus obtained was light in spreadability, and had no stickiness and no change with a lapse of time.

Example 27: Eyeliner

TABLE 18

| | (Components) | (% by mass) |
|---|---|---|
| 1 | Decamethylcyclopentasiloxane | 22.0 |
| 2 | Dimethylpolysiloxane (6 mm$^2$/sec) | 5.0 |
| 3 | Silicone treated black iron oxide | 20.0 |
| 4 | Vitamin E acetate | 0.2 |
| 5 | Jojoba oil | 2.0 |
| 6 | Bentonite | 3.0 |
| 7 | Organopolysiloxane of Example 4 | 2.0 |
| 8 | Ethanol | 10.0 |
| 9 | 1,3-Butylene glycol | 10.0 |
| 10 | Antiseptic | Suitable amount |
| 11 | Perfume | Suitable amount |
| 12 | Purified water | Reminder |

(Manufacturing Method)
A: Components 1 to 2, 4 to 7 were mixed, and Component 3 was added and homogeneously mixed and dispersed.
B: Components 8 to 10 and 12 were mixed.
C: The mixture obtained in B was gradually added to the dispersion obtained in A to emulsify the mixture, then the mixture was cooled and Component 11 was added thereto to obtain an eyeliner.

The eyeliner thus obtained was light in spreadability and easy to draw and had no change with a lapse of time. In addition, it was excellent in water resistance and perspiration resistance on the skin, and cosmetic durability was also extremely good.

Example 28: Suncut Cream

TABLE 19

| | (Components) | (% by mass) |
|---|---|---|
| 1 | Decamethylcyclopentasiloxane | 17.5 |
| 2 | KP545 (Note 1) | 12.0 |
| 3 | Glyceryl triisooctanoate | 5.0 |
| 4 | Octyl paramethoxycinnamate | 6.0 |
| 5 | KSG210 (Note 2) | 5.0 |
| 6 | Organopolysiloxane of Example 1 | 1.0 |
| 7 | Lipophilic-treated zinc oxide | 20.0 |
| 8 | Sodium chloride | 0.5 |
| 9 | 1,3-Butylene glycol | 2.0 |
| 10 | Antiseptic | Suitable amount |
| 11 | Perfume | Suitable amount |
| 12 | Purified water | Reminder |

(Note 1)
KP545; Acrylic silicone (available from Shin- Etsu Chemical Co., Ltd.)
(Note 2)
KSG210; Silicone gel (available from Shin-Etsu Chemical Co., Ltd.)

(Manufacturing Method)
A: Component 2 was added to a part of Component 1 to make it homogeneous, and Component 7 was added to the mixture and dispersed by a bead mill.
B: The remainder of Component 1 and 3 to 6 were mixed, and uniformly mixed.
C: Components 8 to 10 and 12 were mixed and dissolved.
D: The solution obtained in C was added to the mixture obtained in B to emulsify the mixture, and A and Component 11 were added to obtain a sun-cut cream.

The sun-cut cream thus obtained had no stickiness, was light in spreadability, and gave a close contact feeling. There was no change with a lapse of time, and UV effect on the skin was also continued.

Example 29: O/W Hand Cream

TABLE 20

| | (Components) | (% by mass) |
|---|---|---|
| 1 | KP545 (Note 1) | 10.0 |
| 2 | KSG16 (Note 2) | 2.0 |
| 3 | Isoparaffin | 5.0 |
| 4 | Vaseline | 5.0 |
| 5 | Glyceryl triisooctanoate | 3.0 |
| 6 | Organopolysiloxane of Example 1 | 0.5 |
| 7 | Polyoxyethylene sorbitan monooleate | 1.0 |
| 8 | Sepigel 305 (Note 3) | 2.0 |
| 9 | 1,3-Butylene glycol | 5.0 |
| 10 | Glycerin | 5.0 |
| 11 | Antiseptic | Suitable amount |
| 12 | Perfume | Suitable amount |
| 13 | Purified water | Reminder |

KP545; Acrylic silicone (available from Shin-Etsu Chemical Co., Ltd.)
KSG16; Silicone gel (available from Shin-Etsu Chemical Co., Ltd.)
Sepigel 305; (manufactured by SEPPIC)

(Manufacturing Method)
A: Components 1 to 7 were uniformly mixed.
B: Components 8 to 11 and 13 were uniformly mixed.
C: The solution obtained in B was added to the mixture obtained in A to emulsify the mixture, then Component 12 was added to the mixture to obtain an O/W hand cream.

The O/W hand cream thus obtained was light in spreadability, gave an excellent close contact feeling, and effectively protected the skin from water work. Further, there was no change with a lapse of time.

Example 30: O/W Hand Cream

TABLE 21

| | (Components) | (% by mass) |
|---|---|---|
| 1 | KP545 (Note 1) | 10.0 |
| 2 | KP561P (Note 2) | 8.0 |
| 3 | Cetanol | 1.0 |
| 4 | Glyceryl triisostearate | 5.0 |
| 5 | Stearic acid | 3.0 |
| 6 | Glyceryl monostearate | 1.5 |
| 7 | Organopolysiloxane of Example 3 | 0.7 |
| 8 | Sorbitan sesquioleate | 0.5 |
| 9 | Polyoxyethylene sorbitan monooleate | 1.0 |
| 10 | Sodium hydroxide (1% aqueous solution) | 10.0 |
| 11 | 1,3-Butylene glycol | 5.0 |
| 12 | Antiseptic | Suitable amount |

TABLE 21-continued

| | (Components) | (% by mass) |
|---|---|---|
| 13 | Perfume | Suitable amount |
| 14 | Purified water | Reminder |

(Note 1)
KP545; Acrylic silicone (available from Shin-Etsu Chemical Co., Ltd.)
(Note 2)
KP561P; Stearyl-modified acrylic silicone (available from Shin-Etsu Chemical Co., Ltd.)

(Manufacturing Method)
A: Components 1 to 9 were mixed, heated and dissolved.
B: Components 10 to 12 and 14 were heated and mixed.
C: The mixture obtained in B was added to the solution obtained in A to emulsify the mixture, then the mixture was cooled and Component 13 was added thereto to obtain an O/W hand cream.

The O/W hand cream thus obtained had no stickiness, was light in spreadability, gave an excellent close contact feeling, and effectively protected the skin from water work. Further, there was no change with a lapse of time.

It must be stated here that the present invention is not restricted to the embodiments shown by Examples. The embodiments shown by Examples are merely examples so that any embodiments composed of substantially the same technical concept as disclosed in the claims of the present invention and expressing a similar effect are included in the technical scope of the present invention.

The invention claimed is:

1. An organopolysiloxane represented by the following average formula (1),

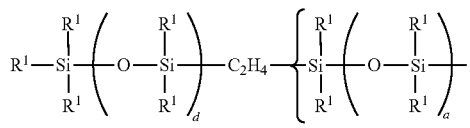

(1)

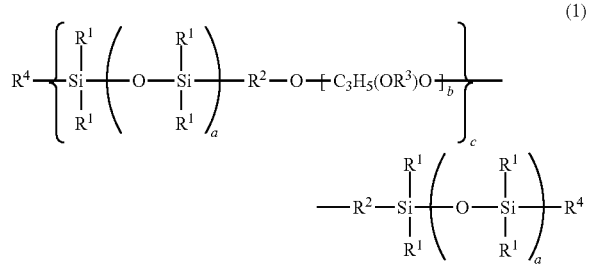

wherein, $R^1$s each independently represent a group selected from an alkyl group having 1 to 30 carbon atoms, a fluorine-substituted alkyl group having 1 to 30 carbon atoms, an aryl group having 6 to 30 carbon atoms, and an aralkyl group having 7 to 30 carbon atoms, $R^2$ represents a divalent organic group having 2 to 15 carbon atoms which may have an oxygen atom(s), $R^3$ represents any of a hydrogen atom and an alkyl group having 1 to 30 carbon atoms, $R^4$s each independently represent an organopolysiloxane represented by the following average formula (2), "a" is 1 to 500, "b" is 1 to 10, "c" is 1 to 10

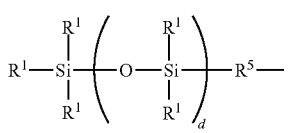

(2)

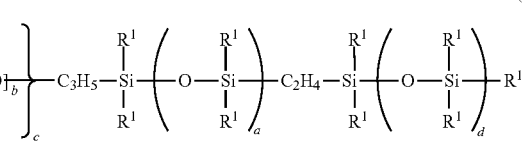

wherein, $R^1$ has the same meaning as defined above, $R^5$ represents a divalent organic group having 2 to 15 carbon atoms, and "d" is 1 to 500.

2. The organopolysiloxane according to claim 1, wherein it is represented by the following average formula (3), (3)

wherein, $R^1$, "a", "b", "c", and "d" have the same meanings as defined above.

3. A cosmetic which comprises the organopolysiloxane according to claim 1 in an amount of 0.1 to 40% by mass based on a total mass of the cosmetic.

4. A cosmetic which comprises the organopolysiloxane according to claim 2 in an amount of 0.1 to 40% by mass based on a total mass of the cosmetic.

5. The cosmetic according to claim 3, wherein the cosmetic further comprises water, and is in a form of an emulsion.

6. The cosmetic according to claim 4, wherein the cosmetic further comprises water, and is in a form of an emulsion.

7. The cosmetic according to claim 3, wherein the cosmetic further comprises any one of silicone oil, ester oil, glyceride oil, and a mixture thereof, and is in a form of a nonaqueous emulsion.

8. The cosmetic according to claim 4, wherein the cosmetic further comprises any one of silicone oil, ester oil, glyceride oil, and a mixture thereof, and is in a form of a nonaqueous emulsion.

9. The cosmetic according to claim 3, wherein the cosmetic further comprises powder, and is in a form of liquid, paste, or solid in which the powder is dispersed.

10. The cosmetic according to claim 4, wherein the cosmetic further comprises powder, and is in a form of liquid, paste, or solid in which the powder is dispersed.

11. A method for manufacturing an organopolysiloxane represented by the following average formula (1) which comprises
subjecting to addition reaction of a dialkenyl(poly)glycerin compound and a both terminal-hydrogen polysiloxane in the presence of a catalyst, under a condition that an amount of Si—H groups contained in the both terminal-hydrogen polysiloxane is in excess of an amount of alkenyl groups contained in the dialkenyl (poly)glycerin compound, and
subjecting to addition reaction of the Si—H group existing at the both terminal of the product obtained by the reaction, and one or more kinds of an organopolysiloxane having an alkenyl group at one terminal thereof, in the presence of a catalyst,

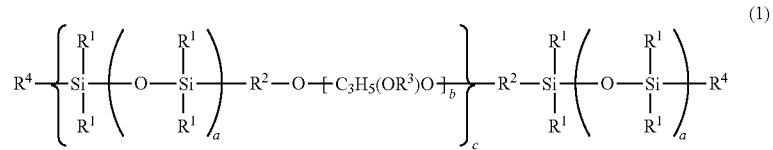

(1)

wherein, $R^1$s each independently represent a group selected from an alkyl group having 1 to 30 carbon atoms, a fluorine-substituted alkyl group having 1 to 30 carbon atoms, an aryl group having 6 to 30 carbon atoms, and an aralkyl group having 7 to 30 carbon atoms, $R^2$ represents a divalent organic group having 2 to 15 carbon atoms which may have an oxygen atom(s), $R^3$ represents any of a hydrogen atom and an alkyl group having 1 to 30 carbon atoms, $R^4$s each independently represent an organopolysiloxane represented by the following average formula (2), "a" is 1 to 500, "b" is 1 to 10, "c" is 1 to 10

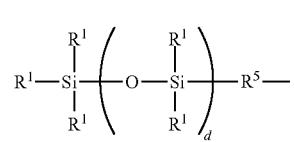

(2)

wherein, $R^1$ has the same meaning as defined above, $R^5$ represents a divalent organic group having 2 to 15 carbon atoms, and "d" is 1 to 500.

* * * * *